United States Patent
Baek et al.

(10) Patent No.: US 12,319,936 B2
(45) Date of Patent: Jun. 3, 2025

(54) NATURAL KILLER CELLS EXHIBITING INCREASED ANTICANCER ACTIVITY AND IMMUNOTHERAPEUTIC USE THEREOF

(71) Applicants: CHA BIOTECH CO., LTD., Seoul (KR); CHA BIOLAB CO., LTD., Seongnam-si (KR)

(72) Inventors: Young Seok Baek, Seongnam-si (KR); In Jee Lee, Seongnam-si (KR)

(73) Assignees: CHA BIOTECH CO., LTD., Seoul (KR); CHA BIOLAB CO., LTD., Seongnam-si (KR)

( * ) Notice: Subject to any disclaimer, the term of this patent is extended or adjusted under 35 U.S.C. 154(b) by 878 days.

(21) Appl. No.: 17/405,230

(22) Filed: Aug. 18, 2021

(65) Prior Publication Data

US 2021/0380945 A1     Dec. 9, 2021

Related U.S. Application Data

(63) Continuation of application No. PCT/KR2020/005136, filed on Apr. 17, 2020.

(30) Foreign Application Priority Data

Apr. 17, 2019 (KR) .................. 10-2019-0045145

(51) Int. Cl.
    *A61K 40/15*     (2025.01)
    *A61K 40/42*     (2025.01)
    *C12N 5/0783*     (2010.01)

(52) U.S. Cl.
    CPC ............ *C12N 5/0646* (2013.01); *A61K 40/15* (2025.01); *A61K 40/42* (2025.01); *A61K 2239/31* (2023.05); *A61K 2239/38* (2023.05); *A61K 2239/47* (2023.05); *A61K 2239/48* (2023.05); *A61K 2239/51* (2023.05); *A61K 2239/59* (2023.05); *C12N 2501/135* (2013.01)

(58) Field of Classification Search
None
See application file for complete search history.

(56) References Cited

U.S. PATENT DOCUMENTS

| | | | |
|---|---|---|---|
| 2009/0123442 A1 | 5/2009 | Dilber et al. | |
| 2018/0312588 A1 | 11/2018 | Wiltzius et al. | |
| 2020/0407685 A1 | 12/2020 | Cho et al. | |

FOREIGN PATENT DOCUMENTS

| | | |
|---|---|---|
| CN | 105008516 A | 10/2015 |
| CN | 106163547 A | 11/2016 |
| CN | 109385403 A | 2/2019 |
| EP | 2476752 A1 | 7/2012 |
| JP | 2017-012010 A | 1/2017 |
| KR | 10-2013-0084465 A | 7/2013 |
| KR | 10-2017-0000798 A | 1/2017 |
| KR | 10-2019-0033458 A | 3/2019 |
| WO | 2017/127729 A1 | 7/2017 |

OTHER PUBLICATIONS

Fernández-Messina L, Reyburn HT, Valés-Gómez M. Human NKG2D-ligands: cell biology strategies to ensure immune recognition. Front Immunol. Sep. 25, 2012;3:299. doi: 10.3389/fimmu.2012.00299. PMID: 23056001; PMCID: PMC3457034. (Year: 2012).*
Barrow, A. et al., "Natural Killer cells control tumor growth by sensing a growth factor," Cell, vol. 172(3): 534-548 (2018).
Parodi, M. et al., "NKp44-NKp44 Ligand Interactions in the Regulation of Natural Killer Cells and Other Innate Lymphoid Cells in Humans," Front. Immunol., vol. 10:719: 10 pages (2019).
Sim, M. et al., "Human NK cell receptor KIR2DS4 detects a conserved bacterial epitope presented by HLA-C," Proc Natl Acad Sci., vol. 116(26):12964-12973 (2019).
Uhlenbrock, F. et al., "Investigations on the Effect of a Platelet Derived Growth Factor-CC Secreting Breast Carcinoma on Natural Killer Cell Cytotoxicity," Degree project in biology, Master of science (2 years) 41 pages (2011).
Foreign Office Action Issued on Oct. 15, 2021 in KR Counterpart Application No. 10-2020-0046826.
Joyce, M.G. and Sun, P.D., "The Structural Basis of Ligand Recognition by Natural Killer Cell Receptors," Journal of Biomedicine and Biotechnology, vol. 2011.
Barrow et al., "Natural Killer cells control tumor growth by sensing a growth factor," Cell, Jan. 25, 2018, vol. 172, No. 3, pp. 534-548, HHS Public Access.
Uhlenbrock, "Investigations on the Effect of a Platelet Derived Growth Factor-CC Secreting Breast Carcinoma on Natural Killer Cell Cytotoxicity," Master's thesis, 2011, Uppsala University.
Gersuk et al., "Inhibition of Human Natural Killer Cell Activity by Platelet-Derived Growth Factor (PDGF) III. Membrane Binding Studies and Differential Biological Effects of Recombinant PDGF Isoforms," J. Immunol. Scand. J. tmmunol, 1991, 33, 521-32.
Barrow et al. "Natural Killer Cells Control Tumor Growth by Sensing a Growth Factor," Cell, Jan. 25, 2018, 172, 534-48.
Esin et al. "Direct Binding of Human NK Cell Natural Cytotoxicity Receptor NKp44 to the Surfaces of Mycobacteria and Other Bacteria," Infection and Immunity, Apr. 2008, 76(4), 1719-27.
Supplementary European Search Report for EP 20791036.5 dated Jan. 3, 2022.

* cited by examiner

*Primary Examiner* — Allison M Fox
*Assistant Examiner* — Qinhua Gu
(74) *Attorney, Agent, or Firm* — United One Law Group LLC; Kongsik Kim; Jhongwoo Peck

(57) ABSTRACT

Provided are a natural killer cell exhibiting increased anticancer activity and immunotherapeutic use thereof. According to the natural killer cell according to an aspect, a relative mean fluorescence intensity (MFI) of a specific receptor significant for cancers including glioblastoma is increased, and thus effective anticancer immunotherapy is possible.

12 Claims, 25 Drawing Sheets

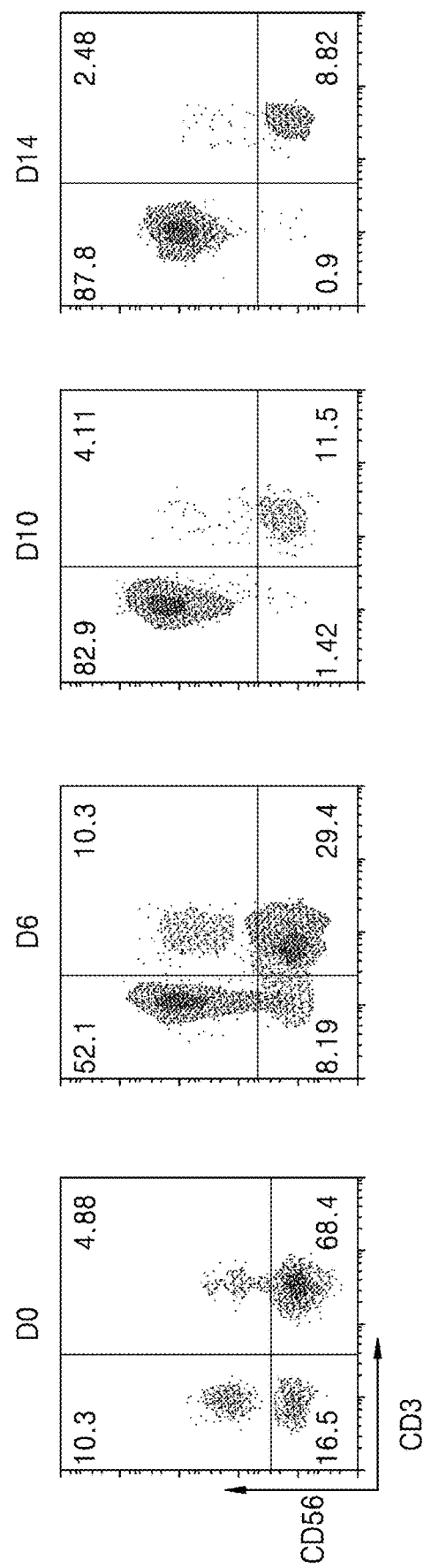

1

NATURAL KILLER CELLS EXHIBITING INCREASED ANTICANCER ACTIVITY AND IMMUNOTHERAPEUTIC USE THEREOF

CROSS-REFERENCE TO RELATED APPLICATIONS

This application is a Continuation of International Application No. PCT/KR2020/005136 filed on Apr. 17, 2020, which claims priority to Korean Application No. 10-2019-0045145 filed on Apr. 17, 2019. The aforementioned applications are herein incorporated by reference in their entireties.

TECHNICAL FIELD

The present disclosure relates to a natural killer cell exhibiting increased anticancer activity and immunotherapeutic use thereof.

BACKGROUND

Natural killer cells (also called "NK cells") used in immune cell therapies are morphologically cells with large granules in the cytoplasm, and account for about 5% to about 15% of lymphocytes in the blood. The main functions of natural killer cells that have been discovered thus far include the ability to kill tumor cells, cytotoxicity to virus-infected cells, ability to kill bacteria and fungi, etc. Therefore, natural killer cells are expected to play an important role in antitumor, immunity, and protective immunity against microorganisms.

Natural killer cells have surface receptors as immune receptors. Since natural killer cells do not have dominant receptors such as the B cell receptor (BCR) of B cells and the T cell receptor (TCR) of T cells, an activation mechanism distinct from other immune cells is expected to exist. In addition, natural killer cells are known as cells having the ability to non-specifically kill cancer. This killing ability of natural killer cells is utilized for solid cancer treatment, together with lymphokine activated killer cells (LAK) and tumor infiltration lymphocytes (TIL), or applied as a new cell therapy for preventing rejection that occurs during bone marrow or organ transplantation by performing immunotherapy through donor lymphocyte infusion (Tilden. A B et al., J. Immunol., 136).

On the other hand, glioma is a malignant tumor that accounts for 60% of primary brain tumors, and until now has had no specific treatment other than radiation therapy. In addition, glioblastoma, which is classified as malignant, has a very high resistance to radiation and chemotherapy, as compared with other cancers, and thus, once diagnosed, the expected survival period is only one year. Malignant glioblastoma accounts for 12% to 15% of all brain tumors, and is the most frequent tumor among single tumors occurring in the brain.

Despite the existing treatment options for patients with cancers including glioblastoma, therapies that may improve efficacy and overcome self-tolerance are being studied, and to this end, there is a need for the development of natural killer cells with increased activity of specific immune receptors.

SUMMARY

An aspect provides a natural killer cell exhibiting increased anticancer activity, the natural killer cell having a receptor expression characteristic of a relative mean fluorescence intensity (MFI) value in a specific range.

Another aspect provides a cell therapeutic agent or a pharmaceutical composition, each including the natural killer cell or a population thereof as an active ingredient.

Still another aspect provides a method of treating cancer, the method including administering an effective amount of the natural killer cell or a population thereof to an individual in need thereof.

An aspect provides a natural killer cell exhibiting increased anticancer activity, the natural killer cell having a receptor expression characteristic of a relative mean fluorescence intensity (MFI) value in a specific range.

As used herein, the term "natural killer cell" or "NK cell" refers to a cytotoxic lymphocyte constituting a major component of the innate immune system, and is defined as large granular lymphocyte (LGL), and constitutes a third kind of cell differentiated from common lymphoid progenitor (CLP) generating B and T lymphocytes. The "natural killer cell" or "NK cell" includes a natural killer cell without additional modification, which is derived from any tissue source, and may include a mature natural killer cell as well as a natural killer progenitor cell. The natural killer cell is activated in response to interferons or macrophage-derived cytokines, and the natural killer cell includes two types of surface receptors controlling cytotoxic activity of cells, marked with "activating receptor" and "inhibitory receptor". The natural killer cells may be generated from hematopoietic cells, for example, hematopoietic stem or precursor cells, placental or umbilical cord-derived stem cells, induced pluripotent stem cells, or cells differentiated therefrom, from any source, for example, a placental tissue, a placental perfusate, umbilical cord blood, placental blood, peripheral blood, spleen, liver, etc.

The natural killer cell may be derived from, for example, a peripheral blood mononuclear cell. The term "peripheral blood mononuclear cell (PBMC)" refers to a mononuclear cell isolated from the peripheral blood of a mammal, specifically, a human, and mainly includes immune cells such as B cells, T cells, and natural killer cells, and granulocytes such as basophils, eosinophils, and neutrophils. The PBMCs may be prepared from peripheral blood collected from a living body by a common preparation method. Specifically, the PBMCs may be isolated from peripheral blood by gradient centrifugation using Ficoll.

In addition, natural killer cells may be obtained by removing red blood cells from a product of leukapheresis, which isolates white blood cells from blood.

In one embodiment, the natural killer cell of the present disclosure may have one or more characteristics selected from the following (a) to (e);

(a) a relative MFI value of NKG2D exhibits a 1.2-fold to 12-fold, 2-fold to 12-fold, 4-fold to 12-fold, 2-fold to 10-fold, 2-fold to 8-fold, 4-fold to 8-fold, 3-fold to 6-fold, or 3.5-fold to 4.5-fold increase, as compared with that on day 0 of PBMC culture;

(b) a relative MFI value of NKp30 exhibits a 1.5-fold to 15-fold, 1.5-fold to 12-fold, 2-fold to 12-fold, 4-fold to 10-fold, 2-fold to 10-fold, 4-fold to 8-fold, 3-fold to 6-fold, or 4-fold to 6-fold increase, as compared with that on day 0 of PBMC culture;

(c) a relative MFI value of NKp44 on day 14 of culture exhibits a 12-fold to 22-fold, 12-fold to 20-fold, 14-fold to 22-fold, 16-fold to 22-fold, 16-fold to 20-fold, 12-fold to 18-fold, 14-fold to 18-fold, or 16-fold to 18-fold increase, as compared with that on day 0 of PBMC culture;

(d) a relative MFI value of ITGA1 exhibits a 1.8-fold to 25-fold, 2-fold to 25-fold, 4-fold to 22-fold, 4-fold to 18-fold, 6-fold to 16-fold, 6-fold to 10-fold, or 6-fold to 8.5-fold increase, as compared with that on day 0 of PBMC culture; and (e) a relative MFI value of ITGA2 exhibits a 1.4-fold to 6-fold, 1.8-fold to 6-fold, 1.8-fold to 5-fold, 2-fold to 5.5-fold, 2-fold to 5-fold, 2-fold to 4-fold, or 2.5-fold to 3.5-fold increase, as compared with that on day 0 of PBMC culture.

The relative MFI value may be an MFI value on day 14 of PBMC culture, relative to that on day 0 of PBMC culture.

As used herein, the term "relative MFI" means a value of the expression intensity of positive cells, relative to that of isotype, and is defined by Equation 1 below.

Relative MFI=Receptor MFI/Isotype MFI      [Equation 1]

The relative MFI is a concept distinct from an expression ratio, which measures an expression ratio of the positive cells relative to the isotype. Even though having the same % of expression ratio, the strength of each receptor function differs depending on the MFI value, and it may be understood that the function is actually increased when the relative MFI value is high.

The present disclosure provides novel natural killer cells treated with a novel material, for example, PDGF-AA, PDGF-BB, PDGF-CC, PDGF-DD, or PDGF-AB, when the natural killer cells are cultured from PBMCs. The novel natural killer cells are different from other known natural killer cells in terms of their preparation methods, and are cells in which relative MFI values of NKG2D, NKp30, NKp44, ITGA1, and ITGA2, which are factors related to anticancer activity and activation of natural killer cells, exhibit an increase from 1.2 times to 30 times those before PBMC culture.

In another specific embodiment, the natural killer cells of the present disclosure may further have one or more characteristics selected from CD16 having an MFI value of 8 to 140, 10 to 140, 8 to 40, 15 to 30, 80 to 140, 100 to 140, or 110 to 130; LFA-1 having an MFI value of 20 to 160, 30 to 160, 30 to 150, 20 to 60, 25 to 50, or 120 to 160, or 135 to 150; NKG2D having an MFI value of 2 to 30, 5 to 30, 5 to 25, 6 to 15, 12 to 30, or 14 to 25; NKp30 having an MFI value of 2 to 25, 5 to 25, 5 to 20, 2 to 14, 7 to 20, or 10 to 18; NKp44 having an MFI value of 10 to 40, 12 to 30, 12 to 25, 14 to 22, 12 to 18, or 18 to 22; ITGA1 having an MFI value of 2 to 30, 4 to 25, 4 to 22, 2 to 16, 4 to 12, 10 to 25, or 14 to 25; ITGA2 having an MFI value of 1 to 10, 1.5 to 10, 2 to 10, 1.6 to 4, 2 to 8, 4 to 8, or 4 to 6; CD2 having an MFI value of 20 to 180; CD27 having an MFI value of 0.1 to 1.5; CD69 having an MFI value of 1 to 10; CD226 having an MFI value of 2 to 12; NKp46 having an MFI value of 2 to 8; CD160 having an MFI value of 0.1 to 4; KIR2DL1 having an MFI value of 0.1 to 4; KR2DL3 having an MFI value of 0.1 to 5; KIR3DL1 having an MFI value of 0.1 to 4; NKG2A having an MFI value of 0.4 to 16; CD161 having an MFI value of 0.2 to 12; CCR3 having an MFI value of 0.3 to 3; CCR5 having an MFI value of 0.5 to 4; CCR6 having an MFI value of 0.8 to 6; CXCR3 having an MFI value of 0.4 to 5; CXCR1 having an MFI value of 0.4 to 5; CXCR2 having an MFI value of 0.1 to 3; and ITGB7 having an MFI value of 1 to 16.

In still another specific embodiment, the natural killer cells of the present disclosure may further have the following characteristics of (f):

(f) an expression level of KIR2DS4 gene on day 14 of culture is at least 10 times or more, specifically, 10 times to 60 times, 10 times to 50 times, 20 times to 40 times, 20 times to 45 times, or 25 times to 40 times that on day 0 of PBMC culture.

In still another specific embodiment, the natural killer cells of the present disclosure may further have the following characteristics of (g) or (h):

(g) a relative MFI value of CD16 on day 14 of culture exhibits a 0.02-fold to 0.85-fold, 0.04-fold to 0.8-fold, 0.08-fold to 0.8-fold, 0.1-fold to 0.6-fold, 0.1-fold to 0.4-fold or 0.12-fold to 0.3-fold decrease, as compared with that on day 0 of PBMC culture, or (h) a relative MFI value of LFA-1 on day 14 of culture exhibits a 0.08-fold to 0.8-fold, 0.1-fold to 0.8-fold, 0.1-fold to 0.7-fold, 0.1-fold to 0.6-fold, 0.2-fold to 0.6-fold, 0.4-fold to 0.6-fold, or 0.2-fold to 0.5-fold decrease, as compared with that on day 0 of PBMC culture.

In still another specific embodiment, the natural killer cells may express any one receptor selected from NKG2D, NKp30, NKp44, CD16, LFA-1, ITGA1, ITGA2, KIR2DS1, KIR2DS2, KIR2DS3, KIRDS4, CXCR1, CXCR2, CXCR3, CCR3, CCR5, CCR6, PSA-NCAM, nestin, tyrosine hydroxylase, CD147, CD127, CD15, CD31, CD146, CD49c, CD107a, NKG2A, CD45, CD140a, and CD11b.

The activating receptors of the natural killer cells mainly recognize ligands whose expression is increased when target cells are in an abnormal state, and causes cytotoxicity to eliminate the target cells.

PSA-NCAM, which is a marker of differentiation ability of nerve cells, may be an indicator related to neuron development and synapse formation in the nervous system during embryonic development, tyrosine hydroxylase may be an enzyme required for synthesizing a neurotransmitter hormone, and CD147, which is a factor related to brain development of an embryo, may have an integrin-mediated adhesion function in the brain endothelium. S100B may improve blood-brain barrier permeability. CD15 may have a function related to chemotaxis, phagocytosis, and/or bactericidal activity, and CD31 may bind to CD38 to heal a wound or to be involved in angiogenesis and cell migration. In addition, CD146, which is a cell surface marker expressed in active T cells, mesenchymal stem cells, etc., may be involved in extravasation of white blood cells, and CD49c may be involved in nerve migration or adhesion between cell-cell and cell-matrix.

NKG2D provides cytotoxic activity by detecting UL16 binding proteins (ULBPs) and MIC A/B, RAE1, H60, and MULT1, which are intracellular molecules whose expression is increased during DNA damage, cancer development, and viral infection.

NKp30 is a receptor activated by binding of extracellular ligands including BAG6, NCR3LG1, and B7-H6, and stimulates cytotoxicity by binding to these ligands.

NKp44 recognizes, as ligands, glycoproteins and proteoglycans on the cell surface, nuclear proteins that may be exposed to the extracellular region, and molecules that are released into the extracellular space or migrate to the extracellular vesicle. Recently, it has been reported that NKp44 recognizes extracellular matrix (ECM)-derived glycoproteins or soluble plasma proteins (e.g., PDGF-DD) such as growth factors (Cell. 2018 Jan. 25; 172(3): 534-548.e19., Front Immunol. 2019; 10: 719.).

KIR2DS4 has been implicated in a number of diseases including cancers, pregnancy disorders, and resistance to HIV. Its exact ligand has not been defined, but KIR2DS4 recognizes a peptide presented by HLA-C*05:01 (e.g., recombinant peptide:HLA-C complex) to activate NK cells, which generate and degranulate TNF-alpha and IFNgamma. Therefore, KIR2DS4 may be a highly peptide-specific activating receptor, and play a sufficient role in immune defense (J Immunol May 1, 2019, 202 (1 Supplement) 177.24;).

ITGA1 is a receptor for laminin and collagen, and is involved in cell-cell adhesion. ITGA1 recognizes some sequences of collagen and is involved in negative regulation of EGF-stimulated cell growth.

ITGA2 is a receptor for laminin, collagen, collagen C-propeptide, fibronectin, and E-cadherin, and is responsible for adhesion to platelets and other cells, collagen regulation, and organization of synthesized extracellular matrix.

At least 50%, 55%, 60%, 65%, 70%, 75%, 80%, 85%, 90%, 95%, 98%, or about 99%, or 50% to 100%, 50% to 90%, 60% to 90%, 60% to 80%, or 60% to 70% of a cell population of the natural killer cells may express NKG2D, NKp30, NKp44, CD16, LFA-1, ITGA1, ITGA2, KIR2DS1, KIR2DS2, KIR2DS3, KIRDS4, CXCR1, CXCR2, CXCR3, CCR3, CCR5, CCR6, PSA-NCAM, nestin, tyrosine hydroxylase, CD147, CD127, CD15, CD31, CD146, CD49c, CD107a, NKG2A, CD45, CD140a, or CD11 b.

Further, at least 50%, 55%, 60%, 65%, 70%, 75%, 80%, 85%, 90%, 95%, 98%, or about 99%, or 50% to 100%, 50% to 90%, 60% to 90%, 60% to 80%, or 60% to 70% of a cell population of the natural killer cells may exhibit any one characteristic selected from KIR2DS1$^+$, KIR2DS2$^+$, KIR2DS3$^+$, KIR2DS4$^+$, CXCR1$^+$, CXCR2$^+$, CXCR3$^+$, CCR3$^+$, CCR5$^+$, CCR6$^+$, PSA-NCAM$^+$, nestin$^+$, CD127$^+$, CD15$^+$, CD31$^+$, CD146$^+$, CD49c$^+$, CD107a$^+$, NKG2A$^+$, CD45$^+$, CD140a$^+$, and CD11 b$^+$.

Further, at least 40%, 45%, 50%, 55%, 60%, 65%, 70%, 75%, 80%, 85%, 90%, 95%, 98%, or about 99%, or 50% to 100%, 50% to 90%, 60% to 90%, or 60% to 80% of a cell population of the natural killer cells may exhibit any one characteristic selected from the group consisting of CD87$^-$, CD10$^-$, and CD80$^-$.

As used herein, the term "positive or +" may mean that, regarding a cell marker, the marker is present in a larger amount or at a higher concentration, as compared with other cells as a reference. In other words, any marker is present inside or on the surface of a cell, and therefore, when a cell may be distinguished from one or more other cell types by using the marker, the cell may be positive for the marker. The term may also mean that a cell has signals of higher intensity than a background intensity, for example, the cell has the marker in an amount enough to be detectable in a cytometry device. For example, cells may be detectably labeled with NKp44-specific antibodies, and when signals from these antibodies are detectably stronger than those of a control (e.g., background intensity), the cells are "NKp44$^+$". As used herein, the term "negative or −" means that although antibodies specific to a particular cell surface marker are used, the marker is not detectable, as compared with the background intensity. For example, when a cell may not be detectably labeled with a CD87-specific antibody, the cell is "CD87$^-$".

In one specific embodiment, the natural killer cells refer to cells in which cytotoxicity, or intrinsic immunomodulatory ability of natural killer cells is activated, or the expression of immune receptors as described above is increased, as compared with parent cells, for example, hematopoietic cells or natural killer progenitor cells. In a specific exemplary embodiment, the natural killer cells are CD3$^-$CD56$^+$. In a specific exemplary embodiment, the activated natural killer cells are CD3$^-$CD56$^+$CD16$^+$. In another specific exemplary embodiment, the activated natural killer cells are additionally CD94$^+$CD117$^+$. In another specific exemplary embodiment, the activated natural killer cells are additionally CD161$^-$. In another specific exemplary embodiment, the activated natural killer cells are additionally NKG2D$^+$. In another specific exemplary embodiment, the activated natural killer cells are additionally NKp46$^+$. In another specific exemplary embodiment, the activated natural killer cells are additionally CD226$^+$. In a specific exemplary embodiment, more than 50%, 60%, 70%, 80%, 90%, 92%, 94%, 96%, or 98% of the activated natural killer cells are CD56$^+$ and CD16$^-$. In another exemplary embodiment, at least 50%, 60%, 70%, 80%, 82%, 84%, 86%, 88%, or 90% of the activated natural killer cells are CD3$^-$ and CD56$^+$. In another exemplary embodiment, at least 50%, 52%, 54%, 56%, 58%, or 60% of the activated natural killer cells are NKG2D$^+$. In another exemplary embodiment, 30%, 20%, 10%, 9%, 8%, 7%, 6%, 5%, 4%, or 3% of the cells are NKB1$^+$. In another specific exemplary embodiment, less than 30%, 20%, 10%, 8%, 6%, 4%, or 2% of the activated natural killer cells are NKAT2$^+$. In a more specific exemplary embodiment, at least 10%, 20%, 25%, 30%, 35%, 40%, 50%, 55%, 60%, 65%, 70%, 75%, 80%, or 85% of the activated CD3$^-$, CD56$^+$ natural killer cells are NKp46$^+$. In another more specific exemplary embodiment, at least 10%, 20%, 25%, 30%, 35%, 40%, 50%, 55%, 60%, 65%, 70%, 75%, 80%, or 85% of the activated CD3$^-$, CD56$^+$ natural killer cells are CD117$^+$. In another more specific exemplary embodiment, at least 10%, 20%, 25%, 30%, 35%, 40%, 45%, or 50% of the activated CD3$^-$, CD56$^+$ natural killer cells are CD94$^+$. In more specific another exemplary embodiment, at least 10%, 20%, 25%, 30%, 35%, 40%, 45%, or 50% of the activated CD3$^-$, CD56$^+$ natural killer cells are CD161$^-$. In more specific another exemplary embodiment, at least 10%, 20%, 25%, 30%, 35%, 40%, 50%, 55%, 60%, 65%, 70%, 75%, 80%, 85%, or 95% of the activated CD3$^-$, CD56$^+$ natural killer cells are CD226+. In more specific another exemplary embodiment, at least 20%, 25%, 30%, 35%, or 40% of the activated CD3$^-$, CD56$^+$ natural killer cells are CD7$^+$. In more specific another exemplary embodiment, at least 30%, 35%, 40%, 45%, 50%, 55%, or 60% of the activated CD3$^-$, CD56$^+$ natural killer cells are CD5$^+$.

In a specific embodiment, the activated natural killer cells or an enriched population of the activated natural killer cells may be assessed by detecting one or more functionally relevant makers, for example, CD94, CD161, DNAM-1, 2B4, NKp46, KIR, and NKG2 family of activating receptors (e.g., NKG2D).

In a specific embodiment, the activated natural killer cell may be generated from the above-described hematopoietic cells. In a specific exemplary embodiment, the activated natural killer cells may be obtained from expanded hematopoietic cells, for example, hematopoietic stem cells and/or hematopoietic progenitor cells. In a specific exemplary embodiment, hematopoietic cells are continuously expanded and differentiated in a first medium without the use of feeder cells. Thereafter, the cells are cultured in a second medium in the presence of feeder cells. Such separation (isolation), expansion, and differentiation may be performed in a central facility, which provides expanded hematopoietic cells for expansion and differentiation at points of use, e.g., hospital, etc.

In a specific embodiment, generation of the activated natural killer cells includes expanding a population of hematopoietic cells. During cell expansion, a plurality of hematopoietic cells within the hematopoietic cell population differentiate into natural killer cells.

As used herein, the term "natural killer progenitor cell", or "NK progenitor cell", or cell population thereof may refer to cells including cells of a natural killer cell lineage, which have not yet developed into mature natural killer cells, or a population thereof, as indicated by, for example, expression levels of one or more phenotypic markers, e.g., CD56, CD16, and KIR. In one exemplary embodiment, the natural killer progenitor cell population includes cells with low CD16 and high CD56. For example, the natural killer progenitor cell population includes about 5%, about 10%, about 15%, about 20%, about 25%, about 30%, about 35%, about 40%, about 45%, or about 50% of $CD3^-CD56^+$ cells. In another specific exemplary embodiment, the natural killer progenitor cell population includes 5%, 10%, 15%, 20%, 25%, 30%, 35%, 40%, 45%, or 50% or less of $CD3^-CD56^+$ cells. In another specific exemplary embodiment, the natural killer progenitor cell population includes 0% to 5%, 5% to 10%, 10% to 15%, 15% to 20%, 20% to 25%, 25% to 30%, 30% to 35%, 35% to 40%, 40% to 45%, or 45% to 50% of $CD3^-CD56^+$ cells.

In a specific embodiment, in the natural killer progenitor cell population, the $CD3^-$ $CD56^+$ cells are additionally $CD117^+$. In a specific exemplary embodiment, in the natural killer progenitor cell population, about 65%, about 70%, about 75%, about 80%, about 85%, about 90%, about 95%, about 98%, or about 99% of the $CD3^-CD56^+$ cells are $CD117^+$. In another specific exemplary embodiment, in the natural killer progenitor cell population, 65%, 70%, 75%, 80%, 85%, 90%, 95%, 98%, or 99% or more of the $CD3^-CD56^+$ cells are $CD117^+$. In another specific exemplary embodiment, in the natural killer progenitor cell population, 65% to 70%, 70% to 75%, 75% to 80%, 80% to 85%, 85% to 90%, 90% to 95%, or 95% to 99% of the $CD3^-CD56^+$ cells are $CD117^+$.

In another specific embodiment, in the natural killer progenitor cell population, the $CD3^-CD56^+$ cells are additionally $CD161^+$. In a specific exemplary embodiment, in the natural killer progenitor cell population, about 40%, about 45%, about 50%, about 55%, about 60%, about 65%, about 70%, or about 75% of the $CD3^-CD56^+$ cells are $CD161^+$. In another specific exemplary embodiment, in the natural killer progenitor cell population, 40%, 45%, 50%, 55%, 60%, 65%, 70%, or 75% or more of the $CD3^-CD56^+$ cells are $CD161^+$. In another specific exemplary embodiment, in the natural killer progenitor cell population, 40% to 45%, 45% to 50%, 50% to 55%, 55% to 60%, 60% to 65%, 65% to 70%, or 70% to 75% of the $CD3^-CD56^+$ cells are $CD161^+$.

In another specific embodiment, in the natural killer progenitor cell population, the $CD3^-CD56^+$ cells are additionally $NKp46^+$. In a specific exemplary embodiment, in the natural killer progenitor cell population, about 25%, about 30%, about 35%, about 40%, about 45%, about 50%, about 55%, about 60%, about 65%, about 70%, about 75%, about 80%, about 85%, about 90% or more of the $CD3^-CD56^+$ cells are $NKp46^+$. In another specific exemplary embodiment, in the natural killer progenitor cell population, about 25%, about 30%, about 35%, about 40%, about 45%, about 50%, or about 55% of the $CD3^-CD56^+$ cells are $NKp46^+$. In another specific exemplary embodiment, in the natural killer progenitor cell population, 25%, 30%, 35%, 40%, 45%, 50%, or 55% or less of the $CD3^-CD56^+$ cells are $NKp46^+$. In another specific exemplary embodiment, in the natural killer progenitor cell population, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90% or more of the $CD3^-CD56^+$ cells are $NKp46^+$. In a more specific exemplary embodiment, in the natural killer progenitor cell population, 25% to 30%, 30% to 35%, 35% to 40%, 40% to 45%, 45% to 50%, or 50% to 55% of the $CD3^-CD56^+$ cells are $NKp46^+$.

Further, for example, the natural killer progenitor cell population is the same as for $CD52^+$, $CD16^+$, $CD244^+$ $CD94^+$, or $CD94^+$, as described above.

In the present disclosure, the natural killer cells may be cultured or genetically engineered such that the above-mentioned receptors are allowed to express or expression or activity thereof is increased.

In the present disclosure, the culture may refer to culture whereby the expression or activity of the above-mentioned receptors is increased from hematopoietic cells, e.g., hematopoietic stem or progenitors from any source, e.g., a placental tissue, a placental perfusate, umbilical cord blood, placental blood, peripheral blood, spleen, liver, etc.

As used herein, the "genetic engineering" or "genetically engineered" refers to a manipulation of introducing one or more genetic modifications into a cell or a cell produced thereby.

As used herein, the term "increase in activity" or "increased activity" may refer to a detectable increase in the activity of a protein or an enzyme. The "increase in activity" or "increased activity" refers to a high level of protein or enzyme activity, as compared with that of a given parent cell, wild-type cell, or cell before culture (e.g., PBMC).

In another specific embodiment, the natural killer cells may be modified or manipulated. The natural killer cells may be genetically modified to have improved target specificity and/or homing specificity.

In another specific embodiment, the natural killer cells may secrete perforin, granzyme, or interferon.

The granzyme may be one or more selected from the group consisting of granzyme A, granzyme B, granzyme H, granzyme K, and granzyme M.

The interferon may be type I interferons (e.g., interferon-α, interferon-β, interferon-κ, or interferon-ω), type II interferons (e.g., interferon-γ), or type III interferons.

Another aspect provides a cell therapeutic agent or a pharmaceutical composition, each including the immune cells or a population thereof as an active ingredient.

The cell therapeutic agent or pharmaceutical composition may be for preventing or treating cancers or infectious diseases.

Still another aspect provides use of the natural killer cells or a cell population thereof in the preparation of pharmaceuticals.

Still another aspect provides a method of treating a disease, the method including administering the natural killer cells or a population thereof to an individual.

As used herein, the term "disease" may refer to a pathological condition, particularly, cancer, an infectious disease, an inflammatory disease, a metabolic disease, an autoimmune disorder, a degenerative disease, a cell death-related disease, or graft rejection.

As used herein, the term "treatment" refers to or includes alleviation, progression inhibition, or prevention of a disease, a disorder, or a pathological condition, or one or more symptoms thereof, and the "active ingredient" or "pharmaceutically effective amount" refers to any amount of the composition used in the practice of the present disclosure provided herein, which is sufficient for alleviation, progression inhibition, or prevention of a disease, a disorder, or a pathological condition, or one or more symptoms thereof.

As used herein, the terms "administering," "introducing", and "implanting" are used interchangeably, and refer to placement of the composition according to a specific embodiment into a subject, by a method or route which results in at least partial localization of the composition according to a specific embodiment at a desired site. The composition may be administered by any appropriate route which results in delivery to a desired location in an individual where at least a portion of the cells or cell component of the composition according to a specific embodiment remain viable. The period of viability of the cells after administration to an individual may be as short as a few hours, e.g., twenty-four hours, to a few days, to as long as several years.

The administration may be co-administration with additional anticancer agents. Examples of the additional anticancer agents may include alkylating agents, antimetabolites, spindle inhibitors, plant alkaloids, cytotoxic/antitumor antibiotics, topoisomerase inhibitors, antibodies, photosensitizers, and kinase inhibitors. Examples of the anticancer agents may include compounds used in targeted therapy and existing chemotherapy. Further, examples of the antibodies may include alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

As used herein, the term "isolated cell", e.g., "isolated natural killer cell" refers to a cell substantially isolated from a tissue from which the cell originates, e.g., peripheral blood.

The composition of the present disclosure may be used to treat or prevent tumors or cancers derived from neoplasm. The neoplasm may be malignant or benign, and the cancer may be primary or metastatic; the neoplasm or cancer may be at an early or late stage. Non-limiting examples of the neoplasm or cancer to be treated may include one or more selected from the group consisting of lung cancer, laryngeal cancer, stomach cancer, colorectal cancer, rectal cancer, liver cancer, gallbladder cancer, pancreatic cancer, breast cancer, ovarian cancer, uterine cancer, cervical cancer, prostate cancer, kidney cancer, skin cancer, bone cancer, muscle cancer, fat cancer, fibrous cell carcinoma, blood cancer, leukemia, lymphoma, multiple myeloma, and glioma.

In addition, the glioma may be astrocytic tumor, oligodendroglial tumor, mixed glioma, or ependymal tumor. More specifically, the astrocytic tumor may be glioblastoma, anticancer drug-resistant glioblastoma, or recurrent glioblastoma.

Without being limited to a specific theory, interactions between PDGF-DD secreted from glioblastoma and NKp44 of natural killer cells have been reported. Further, without being limited to a specific theory, interactions between MICA expressed in glioblastoma and NKG2D of natural killer cells have been reported. Further, without being limited to a specific theory, association between KIR2DS2-positive natural killer cells and glioblastoma has been reported.

Therefore, the natural killer cells according to one specific embodiment may be further effective for cancers (e.g., glioma, glioblastoma, etc.) secreting or expressing MHC class I polypeptide-related sequence A (MICA) or platelet-derived growth factor-DD (PDFG-DD).

Additionally, the natural killer cells according to one specific embodiment may inhibit self-tolerance. Therefore, the natural killer cells according to one specific embodiment may promote immune activation, blood-brain barrier penetration, or cell migration, or may inhibit self-tolerance.

Administration of the pharmaceutical composition according to one specific embodiment may be, but is not particularly limited to, performed via a parenteral route such as intravenously, subcutaneously, intraperitoneally, inhalation, or topical application, or via an oral route. A dosage varies in the range according to a patient's body weight, age, sex, health conditions, diet, administration time, administration method, excretion rate, and severity of disease. A daily dosage refers to an amount of a therapeutic material according to one aspect sufficient to treat disease conditions, which may be ameliorated by administrating the amount to an individual in need of treatment. An effective amount of a therapeutic material may vary depending on a specific compound, disease conditions, and severity thereof, and an individual in need of treatment, which may be routinely determined by one of ordinary skill in the art. For non-limiting example, a dosage of the composition according to one aspect for the human body may vary depending on the patient's age, body weight, sex, a dosage form, health conditions, and disease severity. The composition may be administered, for example, in an amount of about 1,000 cells/time to about 10,000 cells/time, about 1,000 cells/time to 100,000 cells/time, about 1,000 cells/time to 1000,000 cells/time, about 1,000 cells/time to 10,000,000 cells/time, about 1,000 cells/time to 100,000,000 cells/time, about 1,000 cells/time to 1,000,000,000 cells/time, about 1,000 cells/time to 10,000,000,000 cells/time, or about 1,000 cells/time to 100,000,000,000 cells/time, based on an adult patient weighing 70 kg, from once to several times a day at regular time intervals, or may be administered several times at regular time intervals.

The term "individual" refers to a subject in need of treatment of a disease, and more specifically, refers to a mammal, such as human or non-human primates, mice, rats, dogs, cats, horses, cattle, etc.

The pharmaceutical composition according to one specific embodiment may include a pharmaceutically acceptable carrier and/or additive. The pharmaceutical composition may include, for example, sterile water, physiological saline, general buffers (phosphoric acid, citric acid, other organic acids, etc.), stabilizers, salts, antioxidants (ascorbic acid, etc.), surfactants, suspending agents, isotonic agents, preservatives, etc. For topical administration, the pharmaceutical composition may include a combination with organic compounds such as biopolymers, etc., and inorganic compounds such as hydroxyapatite, etc., specifically, collagen matrix, a polylactic acid polymer or copolymer, a polyethyleneglycol polymer or copolymer, and chemical derivatives thereof, etc. When the pharmaceutical composition according to one specific embodiment is formulated into a dosage form suitable for injection, immune cells, or materials increasing activity thereof are dissolved in a pharmaceutically acceptable carrier or frozen in a solution state.

The pharmaceutical composition according to one specific embodiment may appropriately include suspensions, dissolution aids, stabilizers, isotonic agents, preservatives, anti-adhesion agents, surfactants, diluents, excipients, pH adjusting agents, analgesics, buffers, reducing agents, anti-oxidants, etc., depending on its administration method or formulation, as needed. Pharmaceutically acceptable carriers and formulations suitable for the present disclosure, including those mentioned above, are described in detail in a literature [Remington's Pharmaceutical Sciences, 19th ed., 1995]. The pharmaceutical composition according to one specific embodiment may be formulated by using pharmaceutically acceptable carriers and/or excipients according to methods which may be easily carried out by those skilled in the art such that the composition may be prepared as a unit dosage form or incorporated into a multiple dose container. In this regard, its formulation may be in the form of a solution, suspension, or emulsion in an oil or aqueous medium, or in the form of powder, granules, tablets, or capsules.

According to a natural killer cell according to one aspect, a relative mean fluorescence intensity (MFI) of a specific receptor significant for cancers including glioblastoma is increased, and thus effective anticancer immunotherapy is possible.

BRIEF DESCRIPTION OF THE DRAWINGS

FIGS. 1A to 1C show dot plots showing phenotypic analysis of natural killer cells according to culture period (1A: CD3CD56; 1B: CD3CD19, CD14SSC; and 1C: CD3SSC, CD4CD8);

DETAILED DESCRIPTION

Figure 1B:
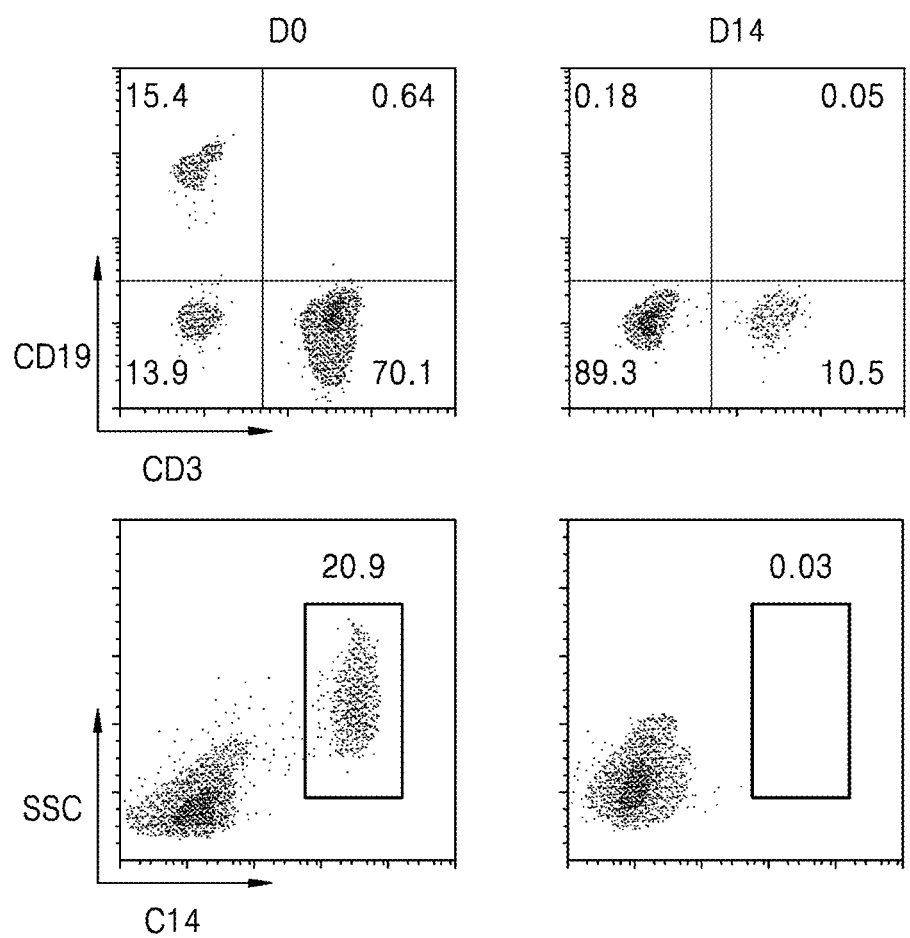

Hereinafter, the present disclosure will be described in more detail with reference to exemplary embodiments. However, these exemplary embodiments are only for illustrating the present disclosure, and the scope of the present disclosure is not limited to these exemplary embodiments.

Example. Preparation of Natural Killer Cells Exhibiting Increased Immune Receptor Activity To prepare natural killer cells expressing immune receptors significant for glioblastoma, natural killer cells were cultured as follows.

1. Preparation of Peripheral Blood Mononuclear Cells 1.1. Isolation of Peripheral Blood Mononuclear Cells (PBMCs) and Plasma from Blood Blood was prepared by collecting blood from the vein of a normal person. At this time, a blood collection tube containing heparin was used as a blood collection container. Each 30 ml of the blood collected from a patient was carefully transferred to two tubes (#352070, BD, or equivalent or higher) containing Ficoll (#17-1440-02, GE Healthcare, or equivalent or higher). The tube containing the blood was centrifuged at 2,500 rpm in a break-off state for 10 minutes, and then the plasma portion of the upper layer was transferred to a new tube. The transferred plasma was inactivated in a heat block for 30 minutes, and then centrifuged at 4,000 rpm for 5 minutes. The supernatant from the centrifuged tube was transferred to a new tube, labeled as plasma, and stored at 2° C. to 8° C.

Plasma was collected from the tube in which the blood and Ficoll were put and centrifuged, and a remaining pale yellow layer in the lower layer was transferred to a new tube while taking care not to mix with a red blood cell layer, and then Ca/Mg-free Dulbecco's phosphate-buffered saline (DPBS) (#14190, Gibco) was added thereto. Then, after centrifugation at 1,500 rpm for 5 minutes, the supernatant was discarded. Precipitated cells remaining after discarding the supernatant were suspended in 5 ml of red blood cell (RBC) lysis buffer (#158904, Qiagen). Thereafter, the cell suspension was centrifuged at 1,500 rpm for 5 minutes to discard the supernatant, and Ca/Mg free DPBS was added to the tube from which the supernatant was discarded, and centrifuged again at 1,500 rpm for 5 minutes. Precipitated cells remaining after discarding the supernatant were suspended in 1 ml of Alys505NK-EX (#01410P10, CSTI) medium.

A small amount of the cell suspension suspended in Alys505NK-EX was taken and diluted 100 times with Ca/Mg free DPBS. Then, a small amount of the diluted solution was taken, and mixed with an equal volume of trypan blue. The mixture was put on a hemocytometer, and the number of cells and viability were determined.

1.2. Freezing of PBMCs

All cell suspensions obtained in Example 1.1 were centrifuged at 1,500 rpm for 5 minutes, and then the supernatant was discarded. Cells were suspended in Cryostor CS10 or a mixture of ALyS505NK-EX+Albumin+DMSO stored at 2° C. to 8° C. such that the number of cells was $1 \times 10^6$ cells/ml to $100 \times 10^6$ cells/ml. 1 mL of the cell suspension was aliquoted into 2 mL cryovials, which were then subjected to a first stage of freezing using a controlled rate freezer (CRF) at 0° C. for 10 minutes to 15 minutes, at −12° C. for 5 minutes to 10 minutes, and −42° C. for 0.5 minutes to 1 minute. After the first stage of freezing, the cryovials were subjected to a second stage of freezing at −25° C. for 1 minute to 3 minutes, and −15° C. for 1 minute to 3 minutes. After the second stage of freezing, the cryovials were subjected to freezing at −42° C. for 20 minutes to 40 minutes, and −120° C. for 20 minutes to 50 minutes. Alternatively, after the first stage of freezing in the range of 4° C. to −40° C. at 3° C./m, the second stage of freezing was performed in the range of −40° C. to −90° C. at 5° C./m, followed by freezing in the range of −90° C. to −120° C. at 5° C./m. The frozen cells were transferred to an $LN_2$ tank and stored (below −130° C.).

1.3. Thawing of Frozen PBMCs

A heat block was set at 37° C., and a culture medium supplemented with 10% plasma was put in a T flask. Depending on the cell density, the volume of the culture medium may be variously adjusted to, for example, 4 ml, 6 ml, 8 ml, or 10 ml. The frozen PBMCs were thawed by putting the cryovials frozen in Example 2.2 into the heat block. When the frozen PBMCs were partially thawed, they were transferred to a T flask containing the culture medium. Subsequently, the T flask was placed in a 5% $CO_2$ incubator at 37° C., and incubated for one day. After collecting the cultured PBMCs in a tube, Ca/Mg free DPBS was added thereto, followed by centrifugation at 1,500 rpm for 5 minutes. Then, the supernatant was discarded. The cells isolated by centrifugation were suspended in a small amount of culture medium, and then the number of cells was counted. Table 1 shows viability after thawing of the cryopreserved cells. As shown in Table 1, 93% or more of PMBCs thawed after cryopreserving according to the present disclosure survived, indicating that high viability was maintained.

TABLE 1

| PBMC viability after thawing | |
|---|---|
| Origin | Viability (%) |
| Donor 1 | 98.07 |
| Donor 2 | 93 |
| Donor 3 | 97.4 |

2. 2.1. Culture of Natural Killer Cells Preparation of Culture Flask Coated with Fibronectin and Gamma Globulin (Primary)

In a 15 ml tube, 0.01 ml of fibronectin (#FC-010, Millipore) and 0.121 ml of a gamma globulin (#020A1004, Green Cross) solution were put, and then 9.859 ml of Ca/Mg free DPBS was added. The prepared coating solution was put into a T75 flask (#156499, Nunc) using a pipette, and allowed to react at 2° C. to 8° C. for 16 hours or more. Before cell culture, the remaining coating solution was washed with Ca/Mg free DPBS and then removed.

2.2. Primary Culture of Natural Killer Cells

The cell suspension prepared in Example 1 was taken and put in the coating flask prepared in Example 2.1, and 1.5 ml of autologous plasma, 0.075 ml of IL-18 (#B003-2, R&D), 0.075 ml of PDGF-DD (1159-SB, R&D), 0.03 ml of anti-NKp46 (#MAB1850, R&D), and 13.4625 ml of Alys505NK-EX (#01410P10, CSTI) were added thereto, followed by incubation in a $CO_2$ incubator for two days to three days. Thereafter, 1.5 ml of autologous plasma and 13.5 ml of Alys505NK-EX were added to the flask, followed by incubation in a $CO_2$ incubator for one day to two days.

2.3. Preparation of Culture Flask Coated with Fibronectin and Gamma Globulin (Secondary)

In a 50 ml tube, 0.025 ml of fibronectin (#FC-010, Millipore) and 0.303 ml of a gamma globulin (#020A1004, Green Cross) solution were put, and then 24.647 ml of Ca/Mg free DPBS was added. The prepared coating solution was put into a T175 flask (#159910, Nunc) using a pipette, and allowed to react at 2° C. to 8° C. for 16 hours or more. Before cell culture, the remaining coating solution was washed with Ca/Mg free DPBS and then removed.

2.4. Secondary Culture of Natural Killer Cells and Treatment with New Function Enhancement Substances After the primary culture in Example 2.2, the T75 flask, in which the cells were cultured, was taken out from the incubator, and the cells were collected and transferred to a T175 flask (#159910, Nunc). 3 ml of plasma, 0.06 ml of anti-NKp46 (#MAB1850, R&D), and 27 ml of Alys505NK-EX (#01410P10, CSTI) were added to the T175 flask, followed by incubation in a $CO_2$ incubator for 1 day to 2 days. Thereafter, the remaining plasma and 0.12 ml of anti-NKp46 solution, 0.03 ml of IL-18, 0.03 ml of PDGF-DD (1159-SB, R&D), 53.85 ml of Alys505NK-EX (#01410P10, CSTI), and one or two or more of 50 ng/ml of PDGF-AA, PDGF-BB, PDGF-CC, PDGF-DD (1159-SB, R&D), and PDGF-AB as new function enhancement substances were added, followed by incubation in a $CO_2$ incubator for 1 day to 2 days.

2.5. Tertiary Culture of Natural Killer Cells

The cells and plasma of the T175 flask incubated in Example 2.4 were put in a culture medium containing 2000 IU/ml of IL-2, followed by incubation in a $CO_2$ incubator. After 2 days to 3 days, an equal volume of fresh culture medium (a culture medium containing 2000 IU/ml of IL-2) was mixed with the cell suspension in which the cells were cultured, followed by incubation in a $CO_2$ incubator.

In the above cultures (all of primary culture, secondary culture, and tertiary culture), instead of using the culture medium supplemented with IL-2, a predetermined amount of IL-2 was added to an immune cell culture medium to which IL-2 was not added.

3. Phenotypic Analysis of Natural Killer Cells According to Culture Period

The activated natural killer cells cultured by the culture method according to the above exemplary embodiment were characterized on days 0, 6, 10, and 14 during the culture period of differentiation and expansion of natural killer cells from PBMCs before culture.

For characterization of the cells, CD3, CD56, CD19, CD16, CD14, CD4, and CD8 were identified as major markers. During the culture period, a percentage of CD3$^-$CD56$^+$ NK cells increased, and on day 14 of culture, NK cells accounted for 85.5% (4.92) as a main component. In addition, CD3$^+$CD56$^-$ T cells decreased to 10% on day 14 of culture, and CD3$^+$CD56$^+$ NKT cells were present at a constant ratio of 5%. Monocytes and B cells were not detected as 0%. In addition, a percentage of CD8⁺ cells was higher than that of CD4⁺ cells among T cells after culture.

Figure 1C:
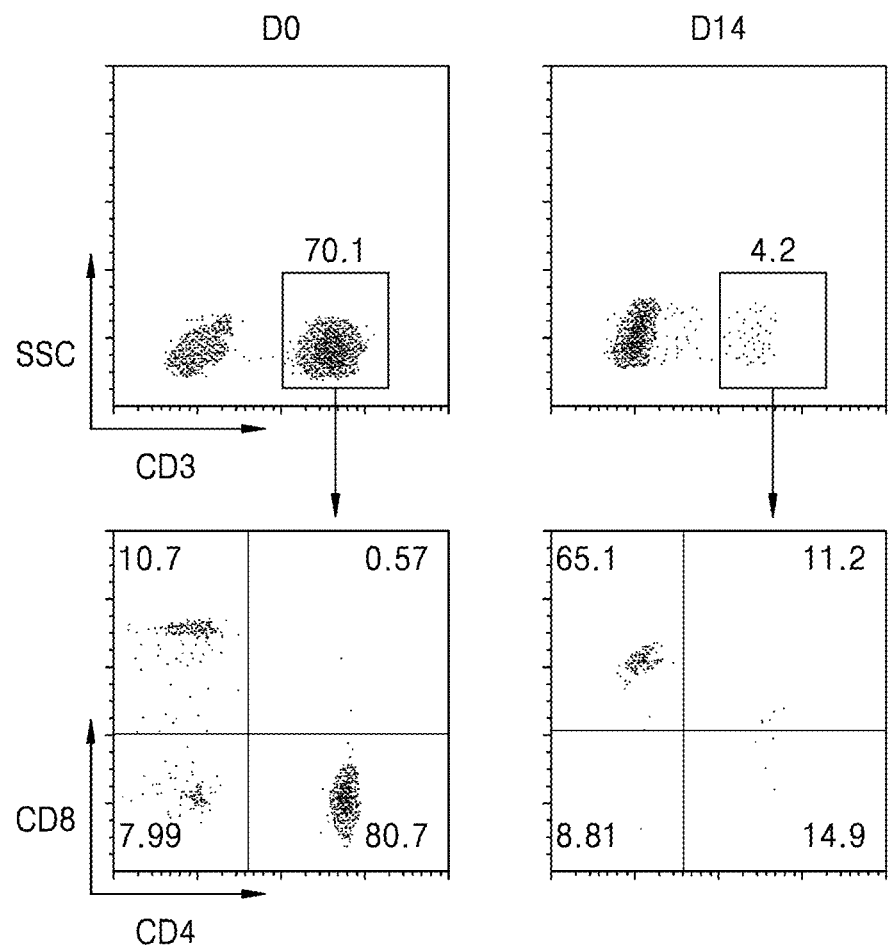

FIG. 1 shows distribution of high-purity natural killer cells, as compared with those before culture.

FIG. 2 shows a graph showing the culture test of 7 people with respect to FIG. 1. (a,b,c,d)

Figure 2A:
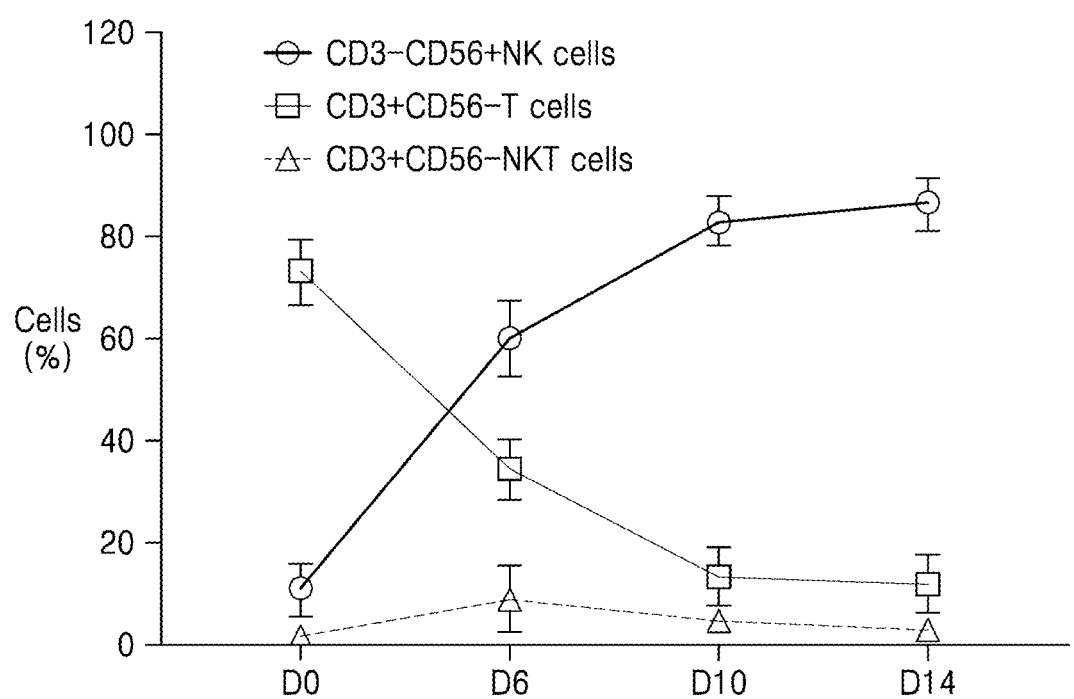
FIGS. 2A to 2F show graphs for results of culture tests of 7 people in FIG. 1, and graphs showing viability and fold expansion of natural killer cells (2A: percentages of $CD3^+$ $CD56^+$, $CD3^-CD56^+$, $CD3^+CD56^-$ cells; 2B: percentages of $CD19^+$ cells; 2C: percentages of $CD14^+$ cells; 2D: percentages of $CD4^+$, $CD8^+$ cells; 2E: fold expansion of natural killer cells; and 2F: cell viability)
Figure 2B:
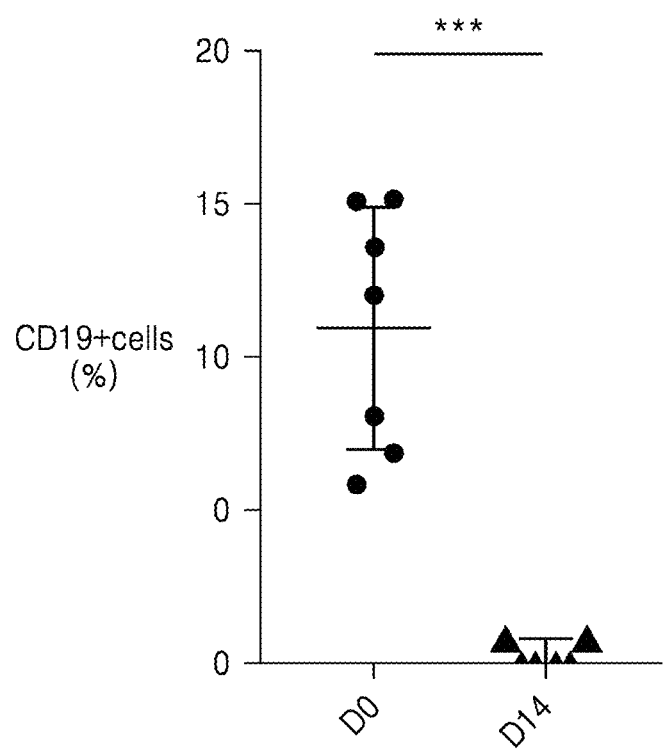
Figure 2C:
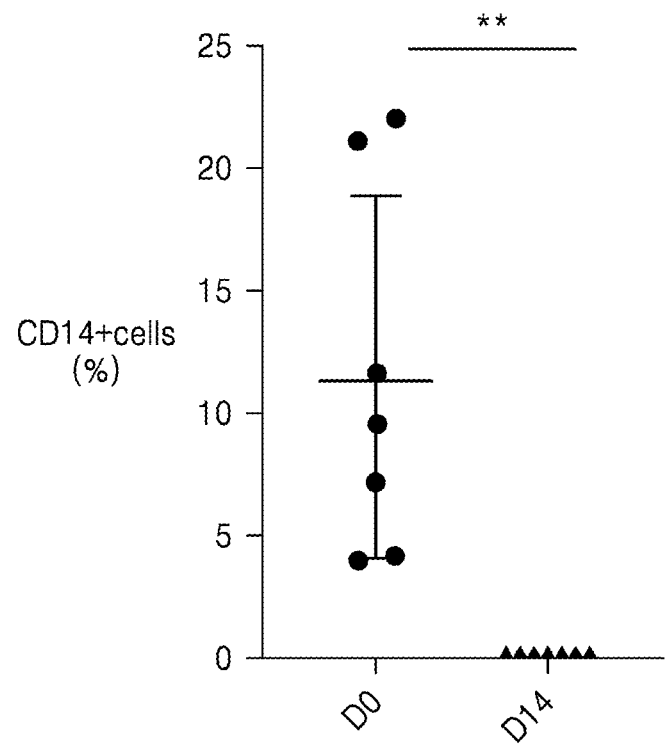
Figure 2D:
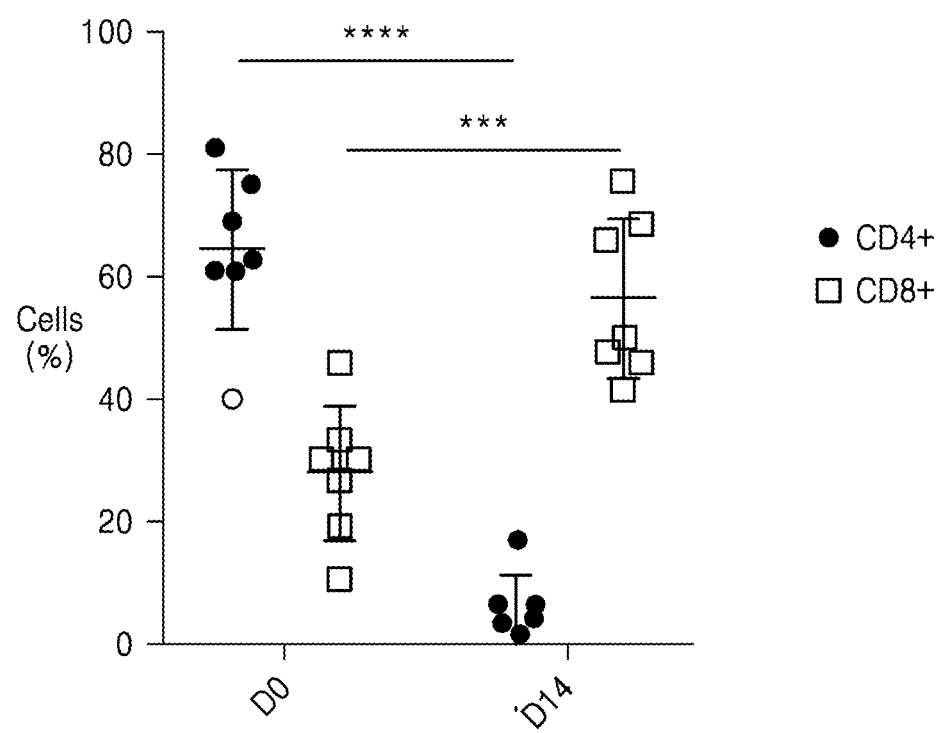
Figure 2E:
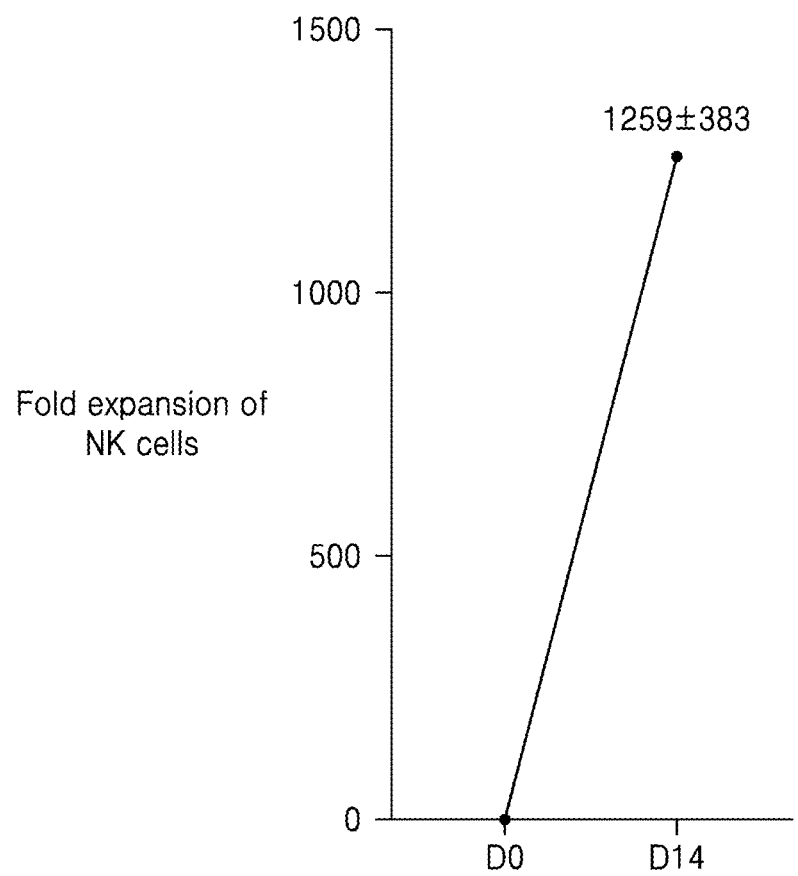
Figure 2F:
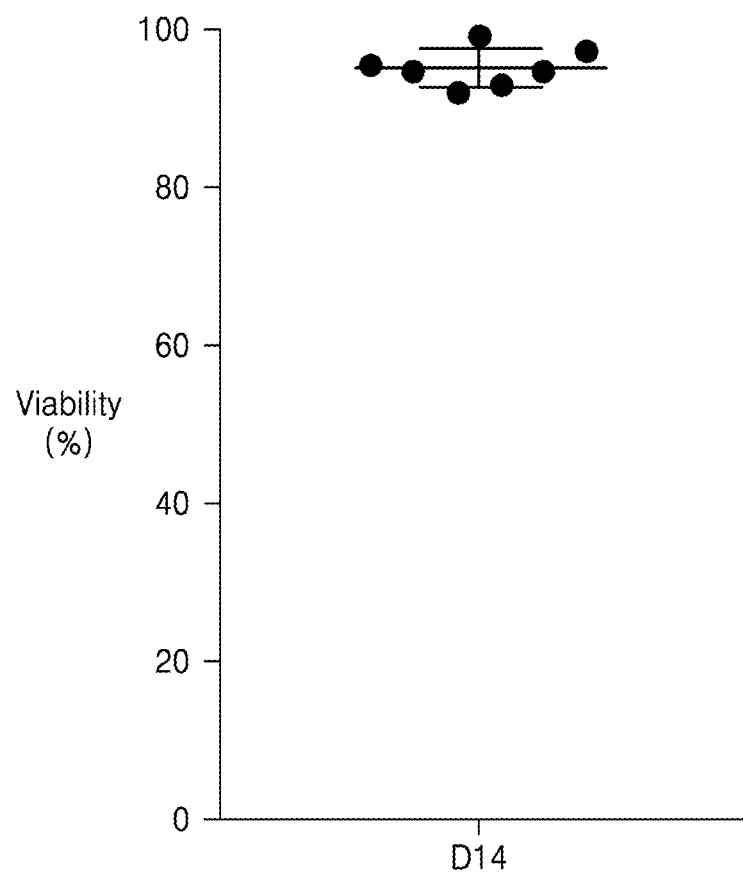

The results of FIGS. 2E and 2F showed that all of the cultures on day 14 maintained high viability of 90% or more, and showed 1259-fold expansion of natural killer cells.

4. Relative MFI Values of NK Cell Receptor Expression Before Culture (D0) and after Culture (D14)

The relative MFI values of activated natural killer cells cultured by the culture method according to the above exemplary embodiments were measured.

The relative MFI means a value of the expression intensity of positive cells, relative to that of isotype, and is defined by Equation 1 below.

Relative MFI=Receptor MFI/Isotype MFI      [Equation 1]

To measure the relative MFI, first, cells before and after culture were collected to prepare $1\times10^7$ cells, which were centrifuged at 1500 rpm for 5 minutes. Then, the supernatant was discarded, followed by dilution with 2 ml of FACS buffer (PBS containing 2% FBS). Antibodies containing fluorescent materials against the substances shown in Table 2 below were put in a 5 ml FACS tube according to each condition, and 100 μl of the diluted cell solution was dispensed and stained in a refrigerator for 30 minutes. After staining, 500 μl of PBS was added, followed by centrifugation at 3200 rpm for 3 minutes. Then, the supernatant was discarded. The pellet of the stained cells was fixed by adding 500 μl of 1% PFA, and then expression of immune receptors of the cells was analyzed using a flow cytometer (Bechman Coulter, USA), and the relative MFI values were determined according to Equation 1 above.

The results of the relative MFI values are shown in Table 2 below.

TABLE 2

Relative MFI (N = 4~5) of natural killer cell receptor

| | | D0 | | | D14 | | |
|---|---|---|---|---|---|---|---|
| Natural killer cell receptor | | Range | Mean | SD | Range | Mean | SD |
| Activating Receptor | CD2 | 67-181 | 117.3 | 51.4 | 27-165 | 115.8 | 60.7 |
| | CD16 | 156-451 | 266.7 | 132.1 | 19-124 | 53.5 | 48.8 |
| | CD27 | 1-1.3 | 1.2 | 0.1 | 0.3-0.9 | 0.7 | 0.3 |
| | CD69 | 0.7-1.5 | 1.2 | 0.4 | 1.4-6.8 | 4.2 | 2.3 |
| | NKG2D | 1.9-5 | 3.4 | 1.3 | 8.4-20.3 | 13.7 | 6.1 |
| | CD226 (DNAM-1) | 1.7-7.9 | 4.1 | 2.7 | 4-7.6 | 5.3 | 1.5 |
| | NKp30 | 1.1-3.6 | 2.5 | 1.1 | 7.2-14.3 | 9.6 | 4.0 |
| | NKp44 | 1-1.2 | 1.1 | 0.1 | 16.3-20.3 | 18.7 | 2.1 |
| | NKp46 | 2.4-4.7 | 3.6 | 1.2 | 3.2-5.5 | 4.2 | 1.2 |
| | LFA-1 | 263-291 | 275.7 | 14.3 | 34-143 | 109.3 | 50.1 |
| | CD160 | 2.2-5.5 | 3.2 | 1.6 | 0.3-1.2 | 0.9 | 0.4 |
| Inhibitory Receptor | CD158a (KIR2DL1) | 1.1-2.1 | 1.4 | 0.4 | 0.3-1.0 | 0.8 | 0.4 |
| | CD158b (KIR2DL3) | 1.1-21.8 | 6.3 | 10.3 | 0.3-1.6 | 1.1 | 0.5 |
| | NKB1 (KIR3DL1) | 1.0-1.3 | 1.1 | 0.2 | 0.3-1.1 | 0.8 | 0.3 |
| | NKG2A (CD159a) | 1.2-1.6 | 1.4 | 0.2 | 0.6-8.0 | 5.7 | 3.5 |
| | CD161 (NKRP1A) | 3.9-6.2 | 4.8 | 1.0 | 0.5-5.0 | 3.2 | 2.0 |
| Chemokine Receptor | CCR3 | 0.8-1.6 | 1.2 | 0.3 | 0.6-0.8 | 0.7 | 0.1 |
| | CCR5 | 1.5-2.1 | 1.8 | 0.2 | 1.0-1.8 | 1.7 | 0.5 |
| | CCR6 | 0.7-1.1 | 8.0 | 5.9 | 1.5-2.3 | 1.9 | 0.4 |
| | CXCR3 | 0.7-1.1 | 1.0 | 0.2 | 0.8-1.4 | 1.1 | 0.3 |
| | CXCR1 | 1.7-4.9 | 2.6 | 1.3 | 0.9-1.6- | 1.2 | 0.2 |
| | CXCR2 | 1.3-7.0 | 3.5 | 2.1 | 0.3-0.9 | 0.5 | 0.3 |
| Integrin Receptor | ITGA1 (CD49a) | 0.9-2.8 | 1.4 | 0.9 | 6.5-21.1 | 13.4 | 6.2 |
| | ITGA2 (CD49b) | 1.1-1.5 | 1.4 | 0.2 | 2.7-5.6 | 4.1 | 1.3 |
| | ITGB7 (CD49d) | 2.0-8.5 | 5.3 | 2.9 | 2.7-7.7 | 5.8 | 2.5 |

The relative MFI is a concept distinct from an expression ratio, which measures an expression ratio of the positive cells relative to the isotype. Even though having the same % of expression ratio, the strength of each receptor function differs depending on the MFI value, and it may be understood that the function is actually increased when the relative MFI value is high.

In this exemplary embodiment, as in 2.5. above, a novel natural killer cell having enhanced function, treated with a novel substance, was prepared, and MFI values of specific receptors thereof were measured to define the characteristics of the novel natural killer cell.

As shown in Table 2, the relative MFI values of NKG2D, NKp30, NKp44, ITGA1, and ITGA2, which are factors related to anticancer activity and activation of natural killer cells, were found to increase from 1.5-fold up to 25-fold. The above results indicate that the natural killer cell treated with the novel substance according to one embodiment is a novel natural killer cell having a specific MFI value and having increased anticancer activity and increased activity of the cell itself.

5. Comparative Analysis of Immune Receptor Expression

Expression of immune receptors was compared and analyzed between activated natural killer cells cultured by the culture method according to the above exemplary embodiments and PBMCs before culture.

Figure 3:
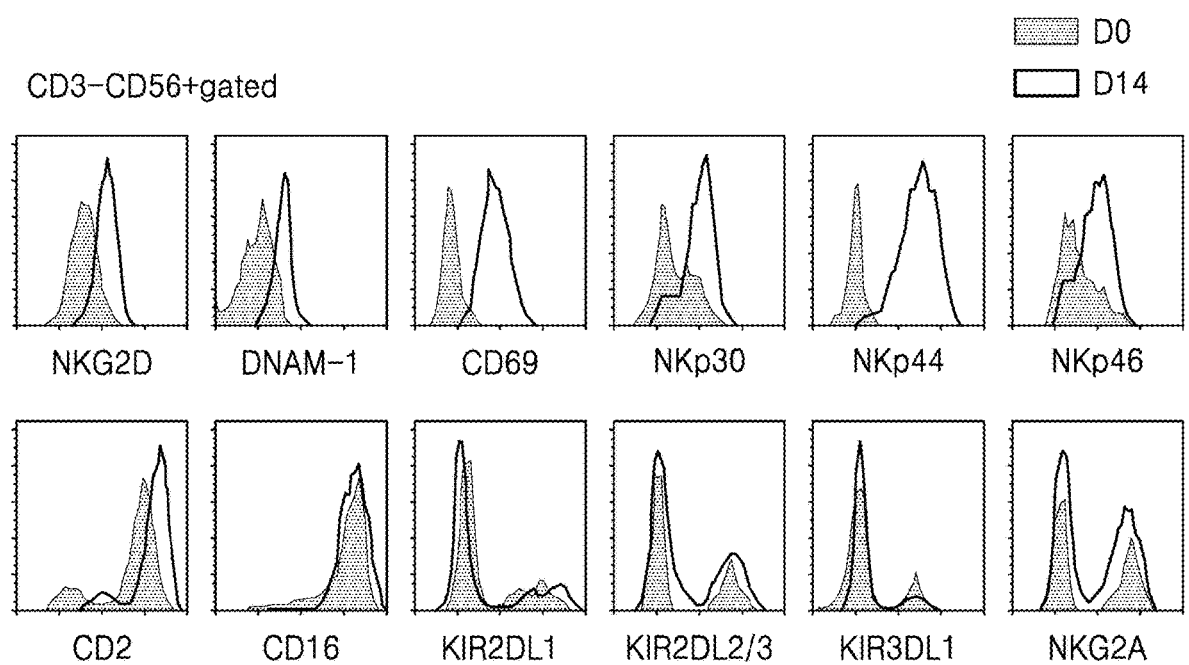
FIG. 3 shows dot plots showing changes in the immune receptor expression of natural killer cells according to one specific embodiment and PBMCs before culture.
Figure 4A:
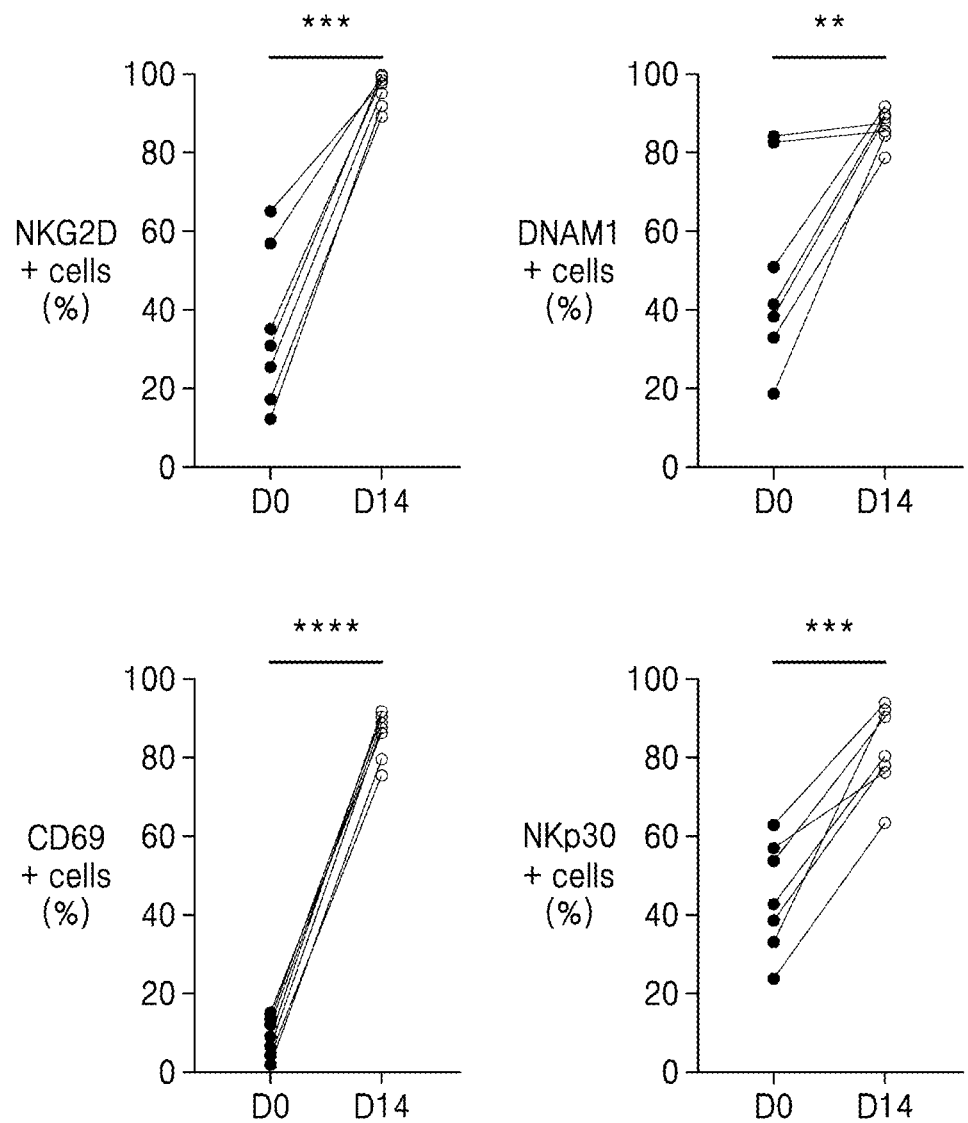
FIGS. 4A to 4C show graphs showing changes in the immune receptor expression of natural killer cells according to one specific embodiment and PBMCs before culture (4A: $NKG2D^+$, $DNAM1^+$, $CD69^+$, $NKp30^+$; 4B: $NKp44^+$, $NKp46^+$, $CD2^+$, $CD16^+$; 4C: $KIR2DL1^+$, $KIR2DL3^+$, $KIRDL1^+$, $NKG2A^+$)
Figure 4B:
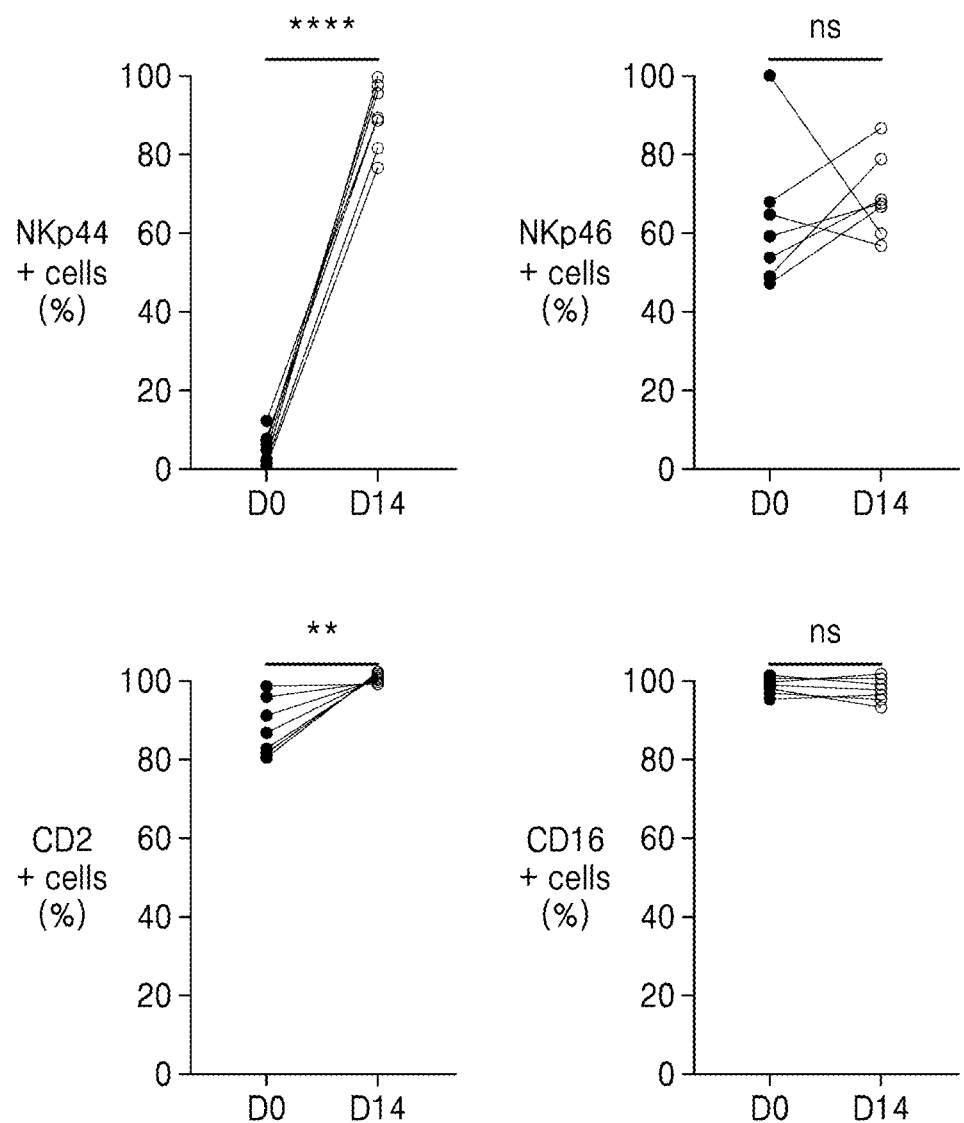
Figure 4C:
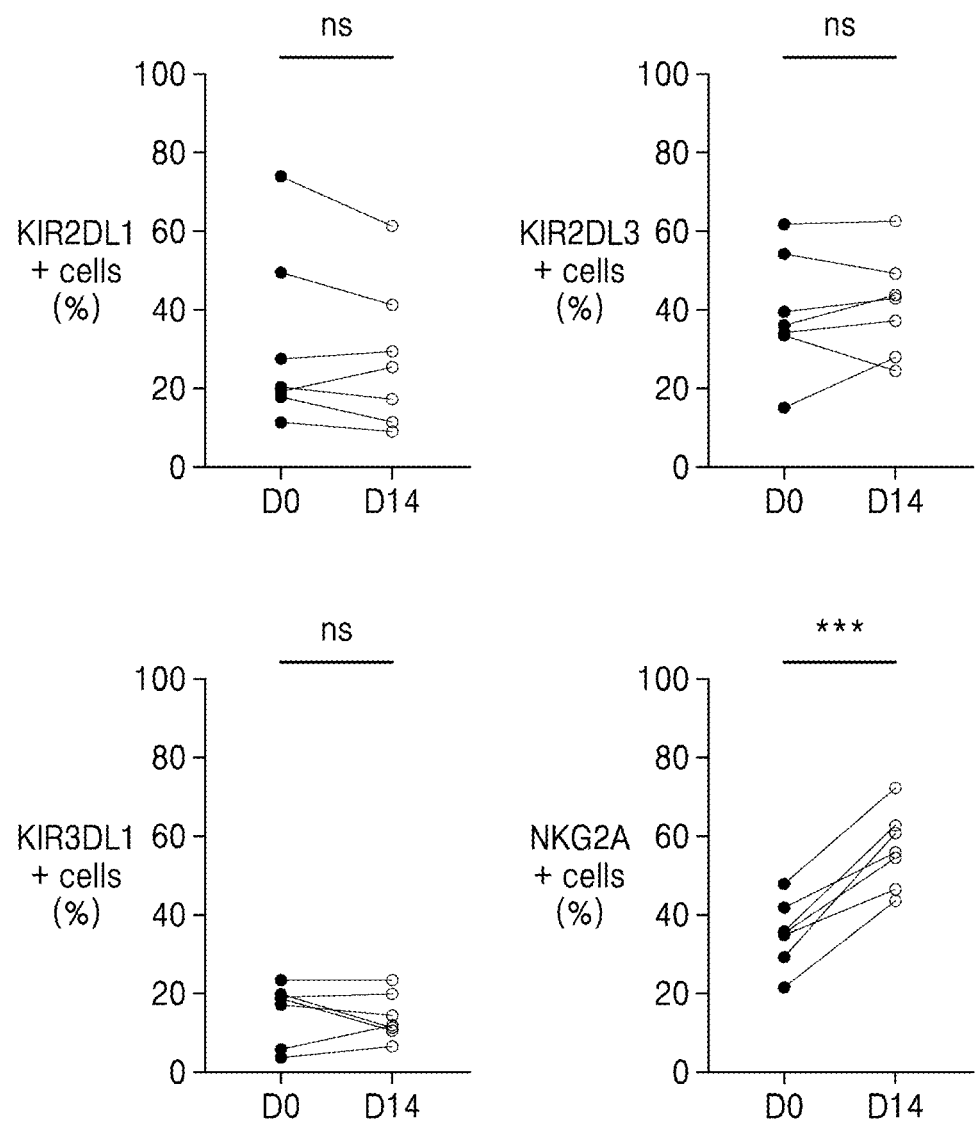

In detail, in the same manner as in 4, expression of the immune receptors of the cells was analyzed using antibodies containing fluorescent materials against the substances shown in Table 3 below, and the results are shown in FIGS. 3 and 4.

TABLE 3

|    | FITC | PE             | APC  |
|----|------|----------------|------|
| 1  | IgG  | IgG            | IgG  |
| 2  | CD3  | CD16           | CD56 |
| 3  | CD3  | CD69           | CD56 |
| 4  | CD3  | NKG2D          | CD56 |
| 5  | CD3  | NKP30          | CD56 |
| 6  | CD3  | NKP44          | CD56 |
| 7  | CD3  | NKP46          | CD56 |
| 8  | CD3  | CD226 (DNAM-1) | CD56 |
| 9  | CD3  | CD158b (KIR2DL3) | CD56 |
| 10 | CD3  | NKB1 (KIR3DL1) | CD56 |
| 11 | CD3  | NKG2A (CD159a) | CD56 |
| 12 | CD3  | CD158a (KIR2DL1) | CD56 |
| 13 | CD3  | CD2            | CD56 |

FIG. 3 shows dot plots of comparing the immune receptor expression between natural killer cells according to one specific embodiment and PBMCs before culture. FIG. 4 shows graphs showing changes in the immune receptor expression of natural killer cells according to one specific embodiment and PBMCs before culture.

As shown in FIGS. 3 and 4, the natural killer cells according to one embodiment showed increased expression of NKG2D, DMAN-1, CD69, CD2, NKp30, NKG2A, and NKp44, and showed little change in the expression of NKp46, CD16, KIR2DL1, KIR2DL2/3, and KIR3DL1, as compared with PMBCs before culture.

6. Analysis of Expression of Factors Related to Brain Tissue and Blood-Brain Barrier Permeability or Cell Migration Promotion of Activated Natural Killer Cells Expression of factors related to brain tissue and blood-brain barrier permeability or cell migration promotion of activated natural killer cells cultured by the culture method according to the above exemplary embodiments was compared and analyzed.

In detail, expression of factors related to brain tissue and blood-brain barrier permeability or cell migration promotion were analyzed in the same manner as in 4, except that antibodies containing fluorescent materials against the substances described in Table 4 below were used, and the results are shown in Table 4.

TABLE 4

|    | Expression marker   | Expression (%) |
|----|---------------------|----------------|
| 1  | PSA-NCAM            | 99.8           |
| 2  | Nestin              | 99.4           |
| 3  | S100B               | 96.9           |
| 4  | Tyrosine Hydroxylase| 89.7           |
| 5  | CD147               | 100            |
| 6  | CD29                | 100            |
| 7  | CD49c               | 99.9           |
| 8  | CD146               | 55.3           |
| 9  | CD15                | 99.1           |
| 10 | CD31                | 57.2           |

7. Analysis of Expression of KIR2DS4 in Activated Natural Killer Cells

The KIR2DS4 mRNA expression pattern of the activated natural killer cells cultured by the culture method according to the above exemplary embodiment was compared with that of PBMCs before culture.

In detail, each RNA was extracted from cells before culture and cells after culture by a trizol isolation method, and total RNA sequencing was performed to identify mRNA expression patterns. The results are shown in Table 5 below.

TABLE 5

| ID | Gene symbol | Fold change (P14 NK cells/ P0 PBMC) |
|------|---------|--------|
| 9513 | KIR2DS4 | 32.562 |

As shown in Table 5, it was found that KIR2DS4 expression was increased about 32-fold in the natural killer cells according to one embodiment, as compared with PBMCs before culture.

Experimental Example 1. Analysis of Anticancer Material Expression

Expression of anticancer materials (granzyme B, perforin, interferon-gamma, and CD107a) of activated natural killer cells cultured by the culture method according to the above exemplary embodiments and PBMCs before culture was compared and analyzed.

First, granzyme B and perforin were analyzed as follows. $5 \times 10^5$ cells were prepared for each sample, centrifuged at 1500 rpm for 5 minutes, and then the supernatant was discarded to obtain a cell pellet. The cell pellet was diluted with 100 μl of FACS buffer, anti-IgG1 k-FITC (ebioscience, 11-4714-42), anti-IgG1k-APC (ebioscience, 17-4714-42), and anti-CD3-FITC (ebioscience, 11-0038-42), anti-CD56-APC (ebioscience, 17-0567-42) antibodies were added to stain surface antigens at room temperature for 15 minutes. Then, 500 μl of PBS was added thereto, followed by centrifugation at 6000 rpm for 3 minutes. For intracellular staining, a fixation/permeabilization solution kit (BD, 554714) was used, and the fixation/permeabilization solution was added and allowed to react in a refrigerator for 20 minutes. A perm/wash buffer was added and centrifuged at 6000 rpm for 3 minutes twice. The cell pellet obtained by discarding the supernatant was diluted in 100 μl of perm/wash buffer, respectively, and anti-IgG1 k-PE (ebioscience, 12-4714-42), anti-Perforin-PE (ebioscience, 12-9994-42), anti-GranzymeB-PE (ebioscience, 12-8899-41) antibodies were added, and intracellular staining was performed in a refrigerator for 30 minutes. After staining, 500 μl of PBS was added to the cell solution, followed by centrifugation. The cells were fixed with 1% PFA, and analyzed using a flow cytometer.

With regard to interferon gamma, cell pellets were obtained in the same manner as above, and then diluted with a culture medium prepared by adding 10% FBS and 1% penicini to an RPMI medium without phenol red, and 500 μl thereof was dispensed in each well of a 24-well plate. Then, cells were treated with 0.5 μl of PMA/Ionomycin (Biolegend) and 0.5 μl of GolgiPlug™ (BD bioscience, USA) and allowed to react in a 5% $CO_2$ incubator at 37° C. for 4 hours. 4 hours after reaction, cells were collected, and centrifuged at 6000 rpm for 3 minutes to discard the supernatant. Surface antigens of the cell pellet were stained with anti-IgG1k-FITC (ebioscience, 11-4714-42), anti-IgG1k-APC (ebioscience, 17-4714-42) and anti-CD3-FITC (ebioscience, 11-0038-42), anti-CD56-APC (ebioscience, 17-0567-42) antibodies, and intracellular staining was performed. Intracellular staining was performed by staining with anti-IgG1k-PE (ebioscience, 12-4714-42) and anti-INF-γ-PE (ebioscience, 12-8899-41) antibodies, followed by fixation with 1% PFA and analysis using a flow cytometer.

Figure 5:
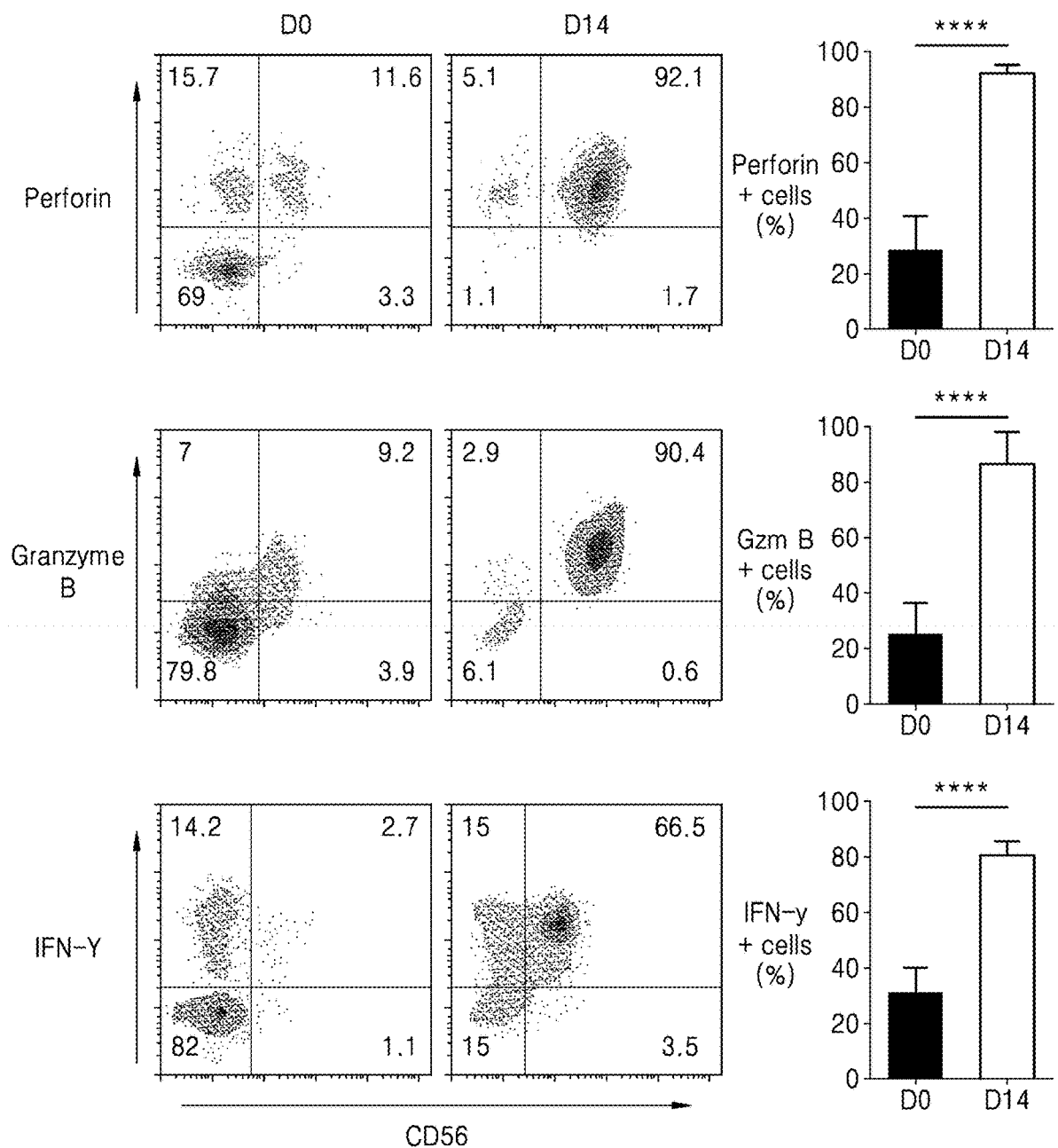
FIG. 5 shows dot plots and graphs showing expression of anticancer materials (granzyme B, perforin, and interferon-gamma) of natural killer cells according to one specific embodiment and PBMCs before culture, as analyzed by flow cytometry.

The results for granzyme B, perforin, and interferon gamma are shown in FIG. 5.

FIG. 5 shows dot plots and graphs showing expression of anticancer materials (granzyme B, perforin, and interferon-gamma) of natural killer cells according to one specific embodiment and PBMCs before culture, as analyzed by flow cytometry.

As shown in FIG. 5, it was found that at least 80% or more of the natural killer cells according to one specific embodiment expressed granzyme B, perforin, and interferon gamma, which are anticancer materials. This is at least 4-fold increase, as compared with that of PBMCs before culture.

In addition, to compare expression of CD107a degranulation between natural killer cells according to one specific embodiment and PBMCs before culture, K562, which is a lymphoblastoid cell extracted from the bone marrow of a chronic myelogenous leukemia patient, was reacted as a target cell, and expression levels of CD107a were analyzed.

In detail, the target K562 cell was prepared at a density of $1 \times 10^5$ cells per condition, centrifuged at 1500 rpm for 5 minutes, and then the supernatant was discarded to obtain a pellet. The cell pellet was diluted by adding 250 μl of a culture medium prepared by adding 10% FBS and 1% penicillin-streptomycin (10,000 U/mL) (gibco, 15140122) to an RPMI medium without phenol red. The natural killer cells were prepared at a density of $1 \times 10^5$ cells per condition to prepare activated natural killer cells and target cells at a ratio of 5:1. After centrifuging the prepared cells, the supernatant was discarded, and 250 μl of the same culture medium as used in dilution of the target cells was added and suspended. Thereafter, the prepared activated natural killer cells and target cells were put in a 24-well plate at a ratio of 5:1, and then anti-IgG1k-PE (ebioscience) and anti-CD107a-PE (ebioscience) antibodies were added, followed by incubation in an incubator under conditions of 37° C. and 5% $CO_2$ for 4 hours. When the reaction was completed in 4 hours, the cells are harvested, and stained with anti-IgG1 k-APC (ebioscience), anti-CD3-FITC (ebioscience), and anti-CD56-APC (ebioscience) with fluorescent materials to identify only natural killer cells. After staining, 500 μl of PBS was added, followed by centrifugation. Then, the cells were washed, and fixed with 1% PFA, and analyzed using a flow cytometer. The results are shown in FIG. 6.

Figure 6:
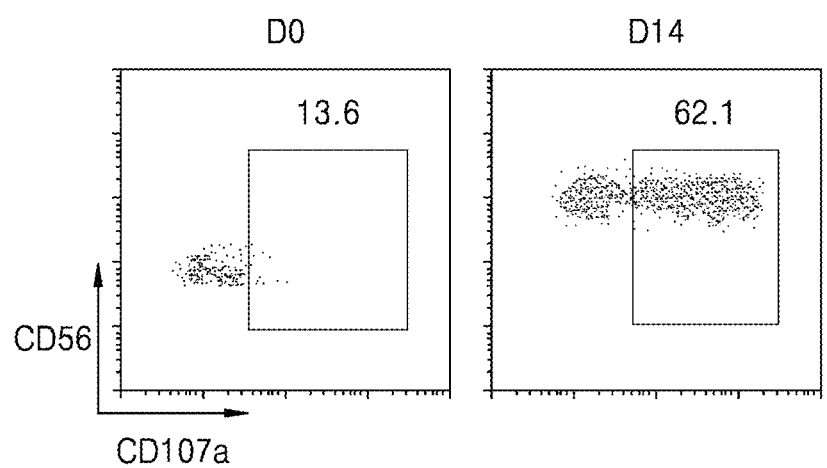
FIG. 6 shows dot plots and graphs showing expression of cd107a degranulation of natural killer cells according to one specific embodiment and PBMCs before culture.
Figure 6:
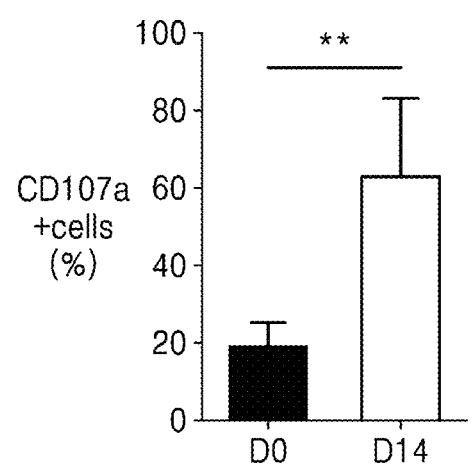
Figure 7A:
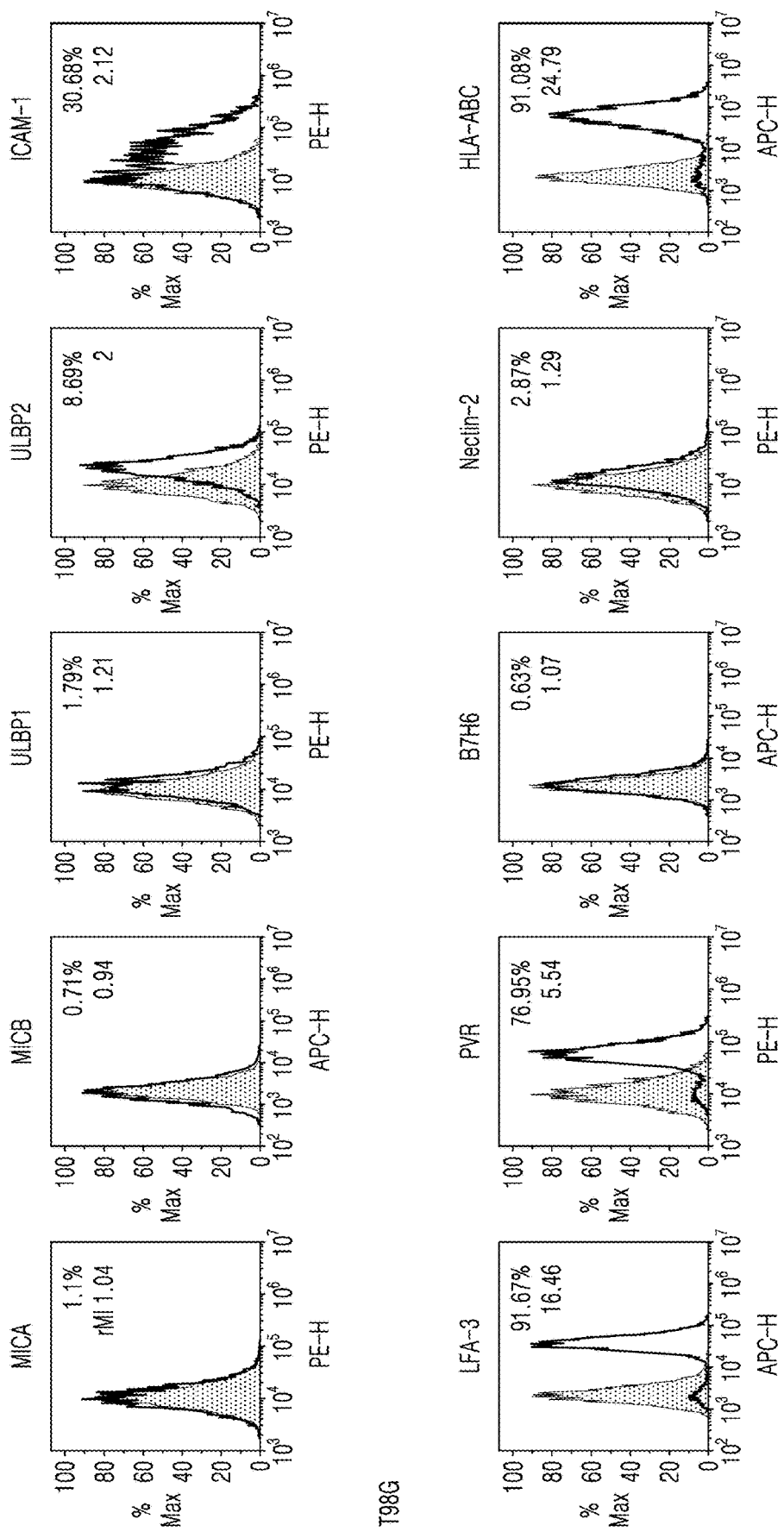
FIGS. 7A to 7D show dot plots showing ligand expression of glioblastoma cell lines for natural killer cells according to one specific embodiment (7A: T98G cell; 7B: U-87MG cell; 7C: A172 cell; and 7D: U-373MG cell)
Figure 7B:
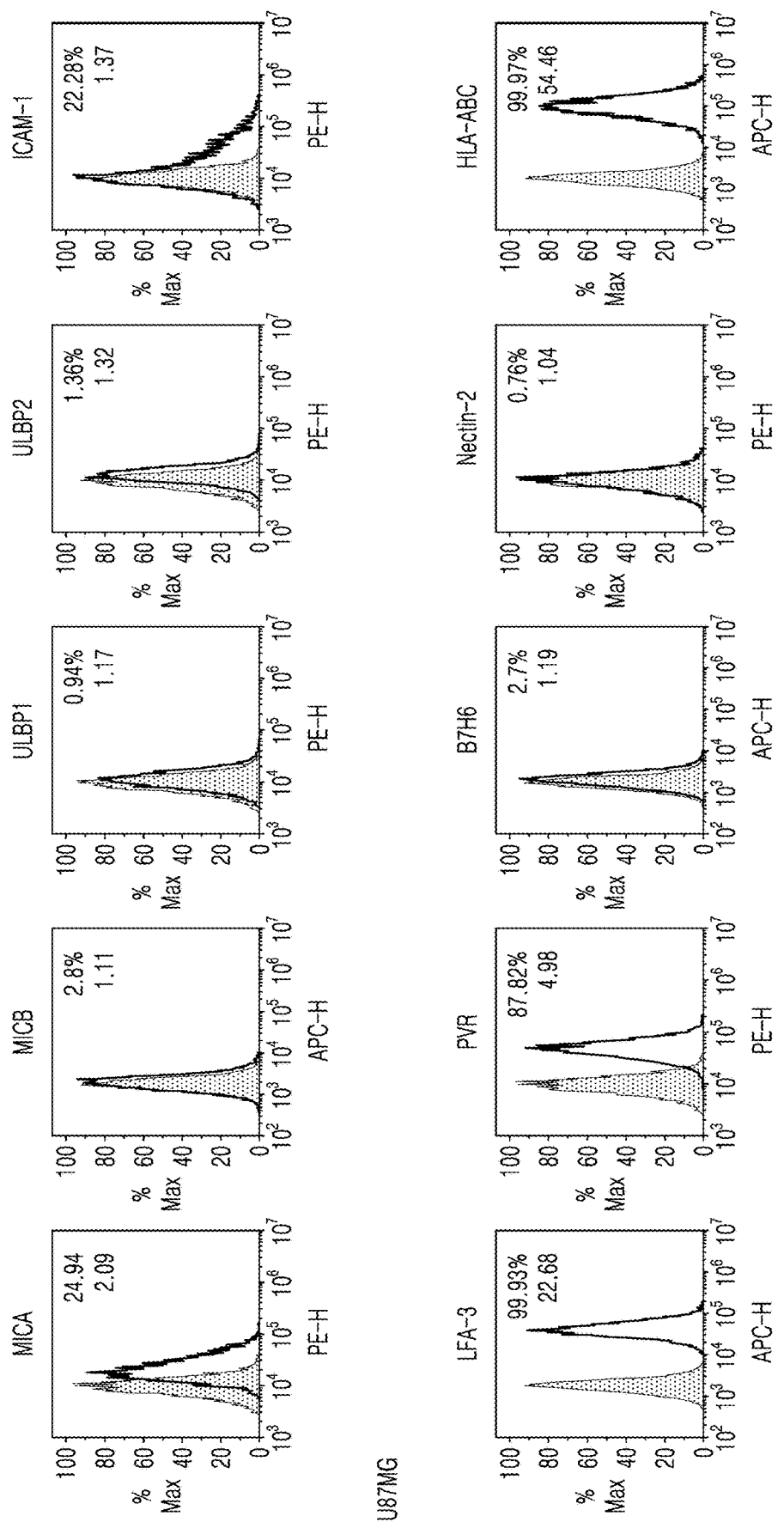
Figure 7C:
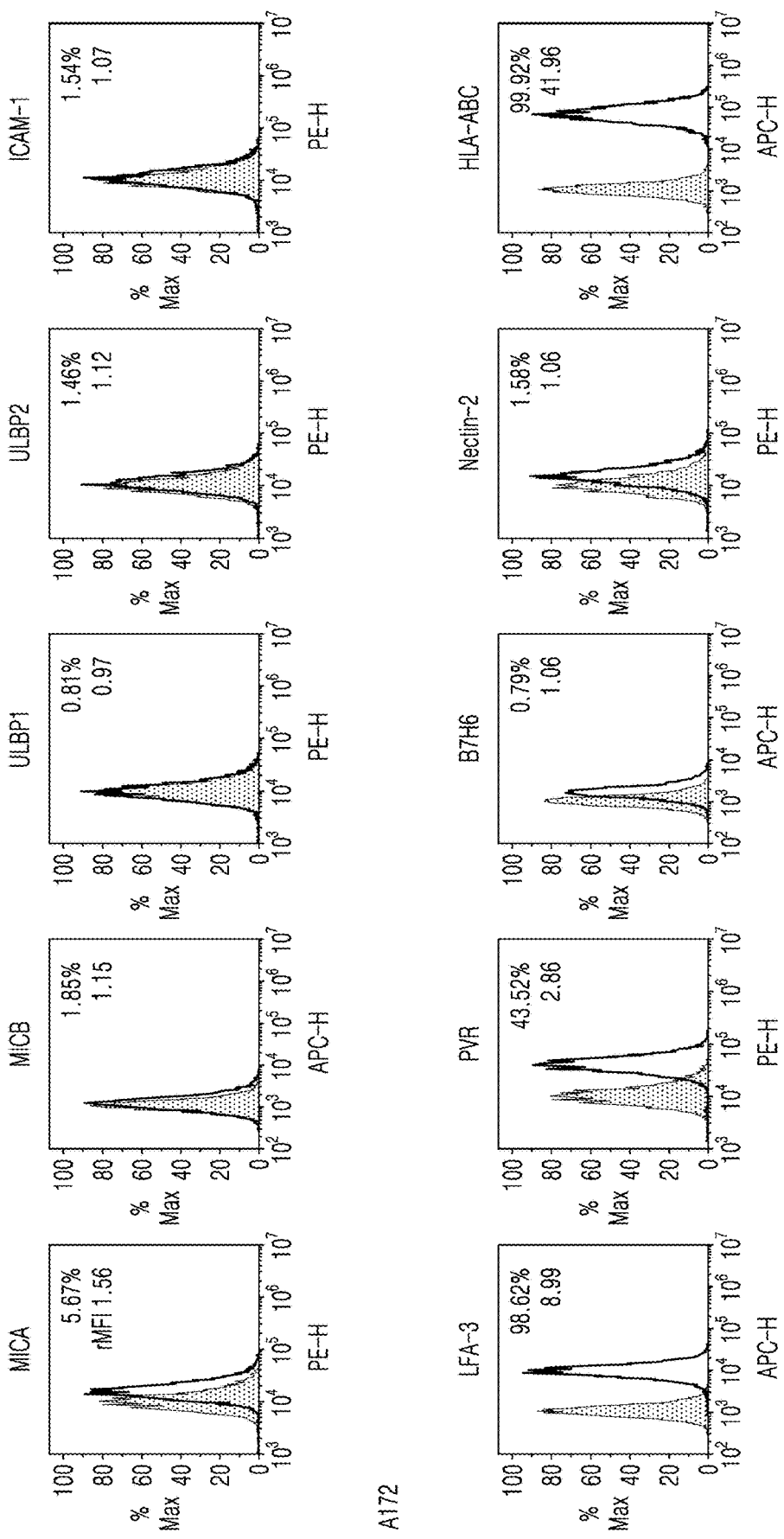
Figure 7D:
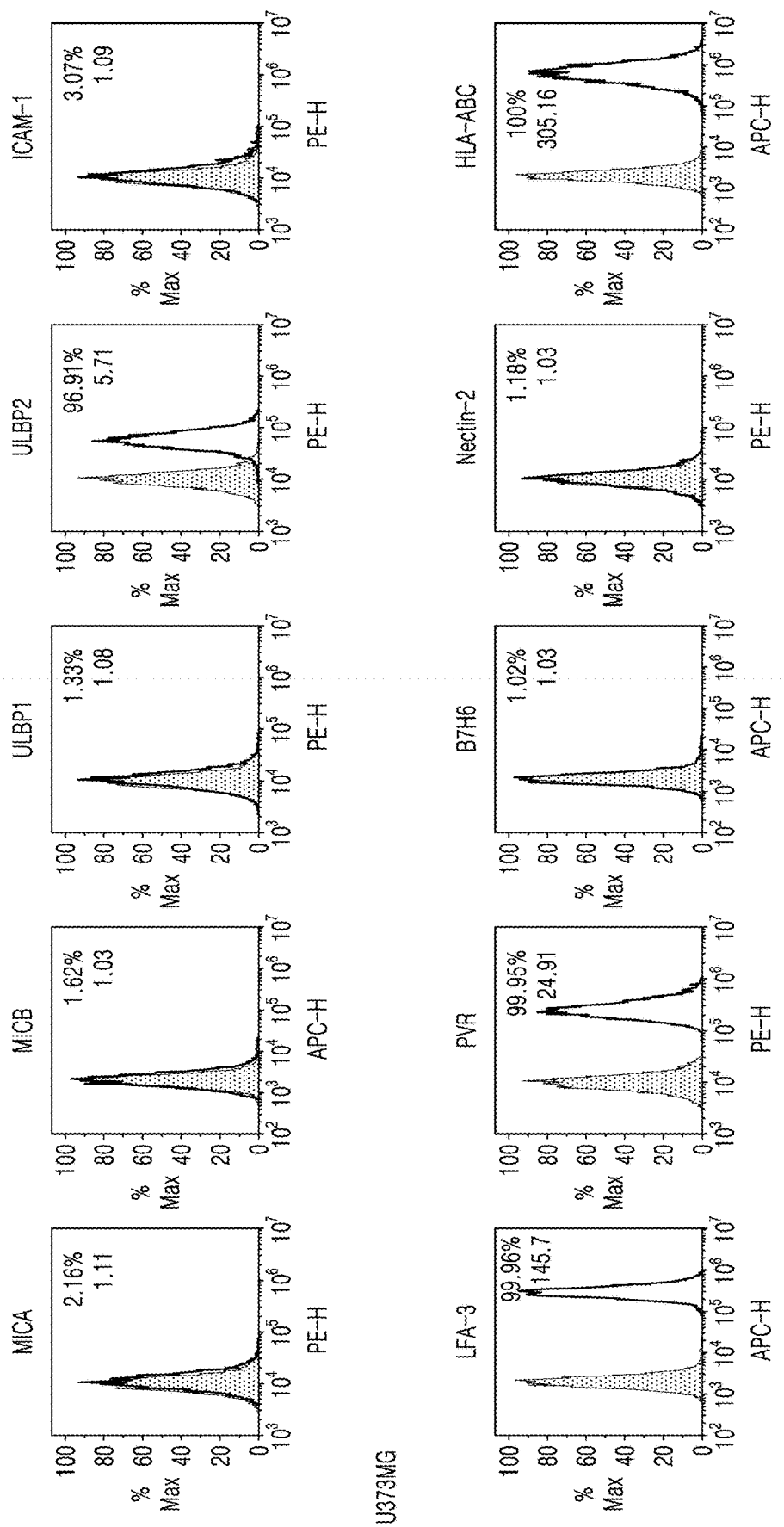

FIG. 6 shows dot plots and graphs showing expression of CD107a degranulation of natural killer cells according to one specific embodiment and PBMCs before culture.

As shown in FIG. 6, it was found that at least 60% or more of the natural killer cells according to one specific embodiment expressed CD107a, which is at least 3-fold higher than that of PBMCs before culture.

Experimental Example 2. Analysis of Interactions Between Ligands of Glioblastoma Cell Lines and Activated Natural Killer Cells Interactions between ligands of glioblastoma cell lines and the natural killer cells according to a specific embodiment were analyzed.

First, U-87MG and T98G cells, which are glioblastoma cell lines, were cultured in a DMEM medium supplemented with 10% FBS and 1% Penicillin-Streptomycin (10,000 U/mL), respectively, and U-373MG and A172 cells, which are another glioblastoma cell lines, were cultured in an RPMI medium supplemented with 10% FBS and 1% penicillin-streptomycin (10,000 U/mL), respectively. Subsequently, staining was performed using antibodies against HLA-ABC, HLA-E, MICA, MICB, ULBP1, ULBP2, ULBP3, ULBP4, PVR, ICAM-1, ICAM-2, ICAM-3, LFA-3, B7-H6, PVR, and Necin-2, which are ligands of T98G, U-87MG, A172, U-373MG glioblastoma cell lines for natural killer cells, and expression levels in the cells were analyzed.

In detail, 0.25% trypsin-EDTA (1×) and phenol red were added to each cancer cell line cultured in a T75 flask, and allowed to react in a 5% $CO_2$ incubator at 37° C. for 3 minutes to 5 minutes, and then the cells were suspended, and harvested by inactivating the enzyme with a culture medium supplemented with 10% FBS. The number of the harvested cells was counted and prepared at a density of $8.5 \times 10^6$ cells, followed by centrifugation at 1500 rpm for 5 minutes. Then, the supernatant was discarded, and the resultant was diluted with 1.7 ml of FACS buffer (PBS containing 2% FBS). Next, the antibodies with fluorescent materials shown in Table 6 below were put into a 5 ml FACS tube according to each condition, and 100 μl of the diluted cell solution was dispensed thereto, and stained at room temperature for 15 minutes. The stained cells were fixed by adding 500 μl of 1% PFA, and then analyzed using a flow cytometer (Bechman Coulter, USA). The results are shown in FIG. 7.

TABLE 6

|    | FITC | PE | APC |
|----|------|-----|-----|
| 1  | IgG | IgG | IgG |
| 2  |     | MICA |    |
| 3  |     |     | MICB |
| 4  |     | ULBP-1 |    |
| 5  |     | ULBP-2 |    |
| 6  |     | ULBP-3 |    |
| 7  |     | ULBP-4 |    |
| 8  |     |     | B7-H6 |
| 9  |     | PVR (CD155) |    |
| 10 |     | Necin-2 (CD112) |    |
| 11 |     |     | LFA-3 (CD56) |
| 12 |     | ICAM-1 (CD54) |    |
| 13 |     | ICAM-2 (CD102) |    |
| 14 | ICAM-3 (CD50) |    |    |
| 15 |     | HLA-E |    |
| 16 |     |     | HLA-ABC |

FIG. 7 shows dot plots showing ligand expression of glioblastoma cell lines for natural killer cells according to one specific embodiment.

As shown in FIG. 7, T98G is a glioblastoma cell with temozolomiede resistance, and U-373MG and U-87MG are grade III and IV glioblastoma cell lines, respectively. Through the ligand analysis for the cells, cytotoxicity through interaction with major receptors of NK cells may be expected. In particular, more significant results may be expected in T98G (rMFI 24.8) and U-87MG (rMFI 30.5), which have low HLA-ABC expression and relatively high NK ligand expression.

Experimental Example 3. Examination of Cytotoxicity Against Glioblastoma Cell Lines To examine the direct cytotoxicity of the natural killer cells according to one specific embodiment, a blood cancer cell line K562, and glioblastoma cell lines A172, U-87MG, U-373MG, and T98G cells, which have high sensitivity to natural killer cells, were subjected to a cytotoxicity test.

Target cancer cells (K562, U-87MG, U-373MG, A172, T98G) were collected, and centrifuged at 1500 rpm for 5 minutes, respectively. Each supernatant was discarded. Then, each cell pellet was diluted with DPBS and washed, and the cell pellet after washing was suspended in a culture medium prepared by adding 10% FBS to an RPMI medium without phenol red. $1 \times 10^5$ cells per condition were prepared, and stained with CFSE (Life technologies) at a concentration of 5 μM by incubating for 10 minutes in an incubator under 5% $CO_2$ conditions. The cells were washed with DPBS twice, and diluted with a culture medium prepared by adding 10% FBS to an RPMI medium without phenol red. Activated natural killer cells were prepared according to E:T ratios to the target cells (1:1, 1.25:1, 2.5:1, 5:1, 10:1, 20:1), and dispensed, together with the target cells, in a 24-well plate, and mixed. The cells were reacted for 4 hours, and treated with 7-aminoactinomycin D (7AAD) 20 minutes before the end of the reaction. After the reaction was completed, the cells were collected in a 5 ml FACS tube, and the cytotoxicity of the cells was analyzed through a flow cytometer. The results are shown in FIGS. 8 and 9.

Figure 8:
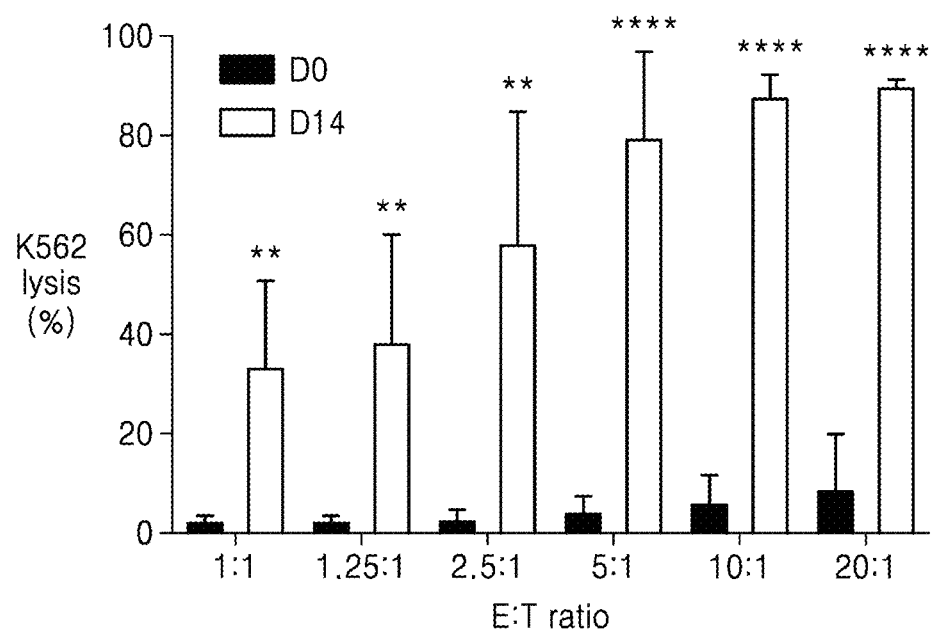
FIG. 8 shows cytotoxicity of natural killer cells according to one specific embodiment against a blood cancer cell line K562 according to E:T ratios.

FIG. 8 shows cytotoxicity of natural killer cells according to one specific embodiment against the blood cancer cell line K562 according to E:T ratios.

Figure 9:
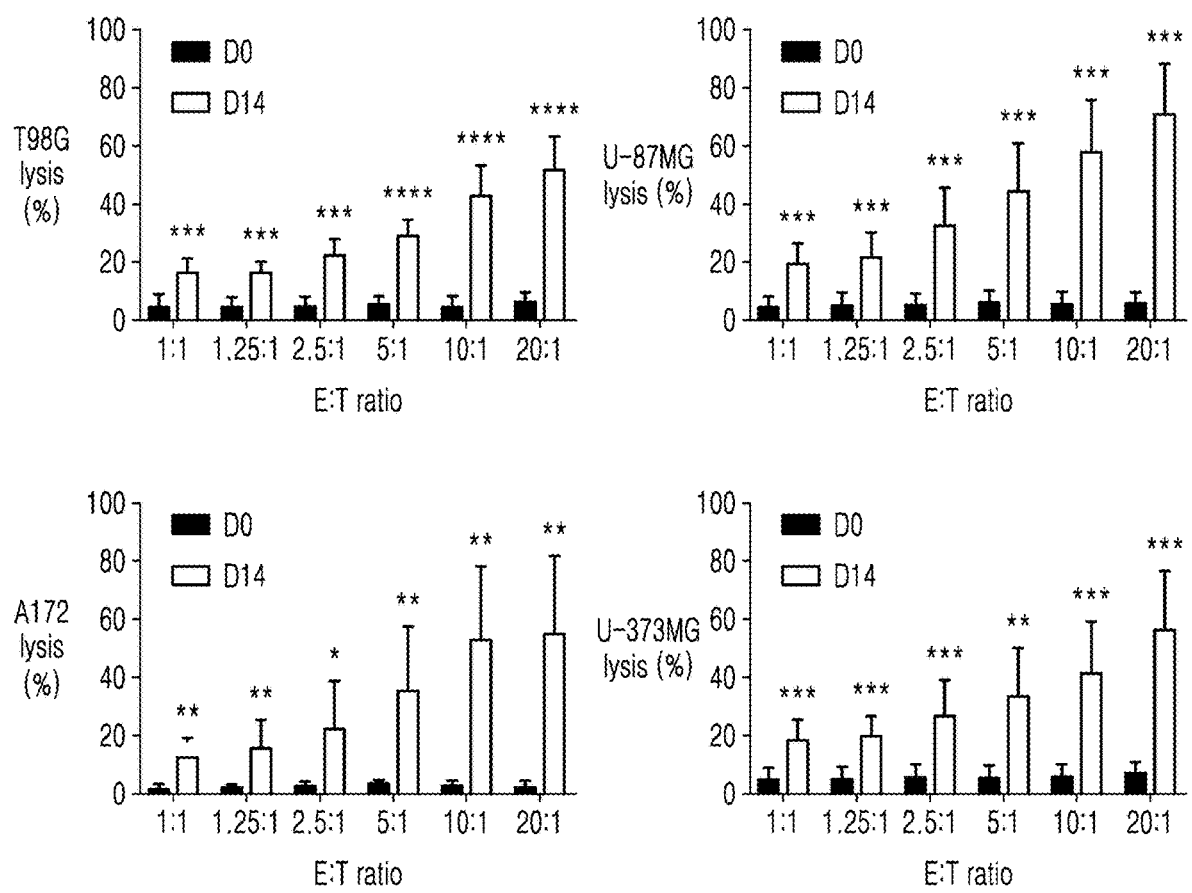
FIG. 9 shows cytotoxicity of natural killer cells according to one specific embodiment against glioblastoma cell lines A172, U-87MG, U-373MG, and T98G according to E:T ratios.

FIG. 9 shows cytotoxicity of natural killer cells according to one specific embodiment against glioblastoma cell lines A172, U-87MG, U-373MG, and T98G according to E:T ratios.

As shown in FIGS. 8 and 9, it was confirmed that PBMCs before culture showed no significant anticancer activity against glioblastoma, whereas the natural killer cells according to one specific embodiment showed significant anticancer activity against the blood cancer cell line and the glioblastoma cell lines.

These results suggest that the novel natural killer cell according to one specific embodiment not only expresses significant immune receptors for glioblastoma, but also expresses immune receptors capable of overcoming self-tolerance, and thus may be usefully applied to the treatment of blood cancer, glioblastoma, etc.

Experimental Example 4. Blocking Assay of Natural Killer Cells

It was examined whether cytotoxicity against cancer cells is inhibited when expression of specific factors is suppressed in the natural killer cells according to one specific embodiment.

In detail, an antibody against NKp30, an antibody against NKp44, and an antibody against NKG2D were used to prepare natural killer cells in which the activities of these receptors were blocked. Thereafter, in the same manner as in Experimental Example 3, cytotoxicity against U-87MG, U-373MG, A172, and T98G was examined, and the results are shown in FIG. 10.

Figure 10:
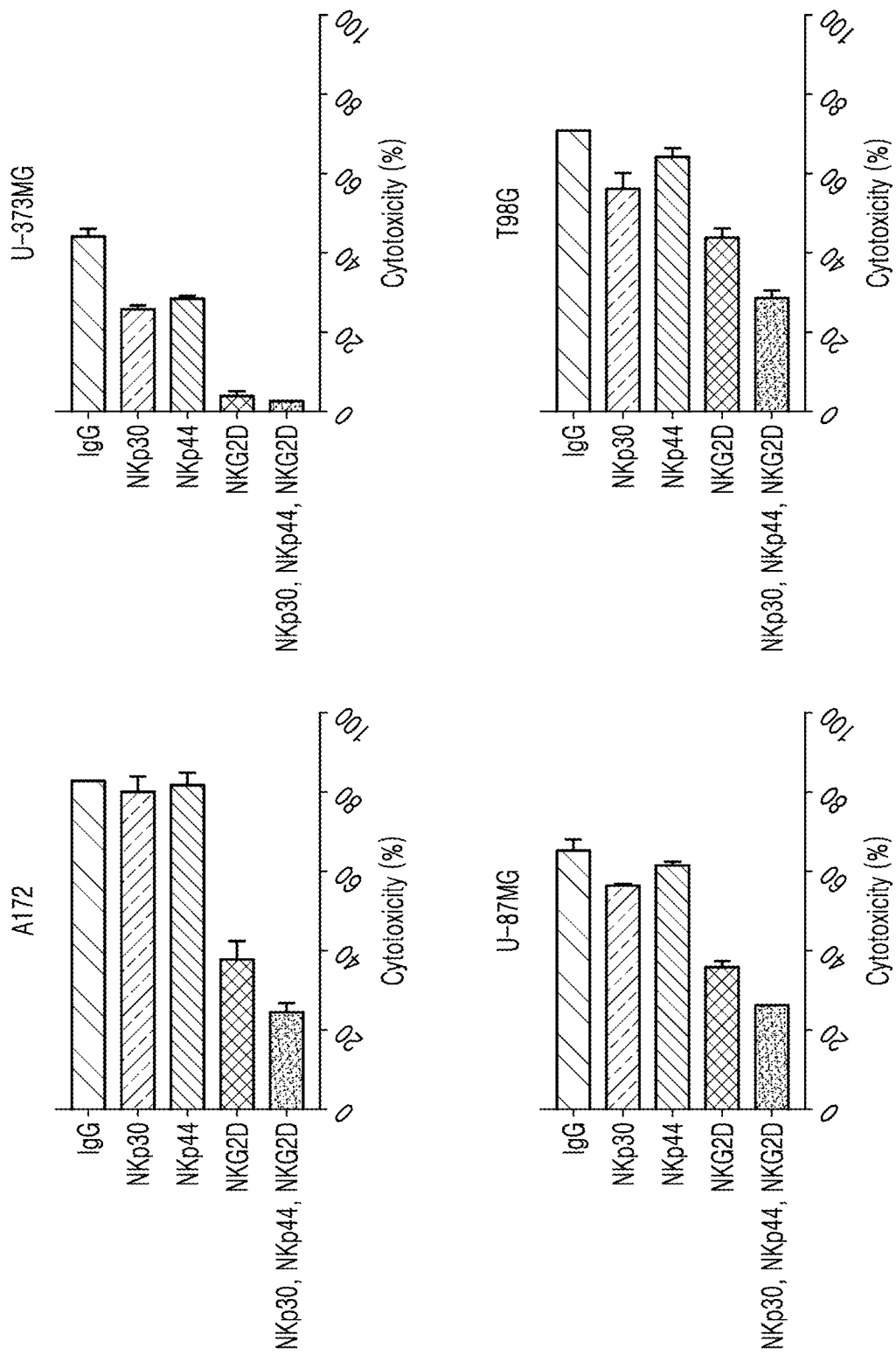
FIG. 10 shows graphs showing cytotoxicity of natural killer cells according to one specific embodiment against cancer cell lines, after blocking specific receptors in the natural killer cells.

FIG. 10 shows graphs showing cytotoxicity of natural killer cells according to one specific embodiment against cancer cell lines, after blocking specific receptors in the natural killer cells.

As shown in FIG. 10, it was found that when the activity of NKp30, NKp44, or NKG2D was inhibited in the natural killer cells according to one specific embodiment, cytotoxicity was remarkably reduced. In particular, it was found that when the activity of NKG2D was inhibited, or when activities of all three receptors were inhibited, the cytotoxicity was remarkably inhibited.

These results indicate that the activity of NKp30, NKp44, and/or NKG2D in the natural killer cells according to one specific embodiment is a major factor for cytotoxicity, and the natural killer cells having a specific MFI value of NKp30, NKp44, and/or NKG2D according to one specific embodiment are cells with remarkably increased anticancer activity.

Experimental Example 5. Analysis of Anticancer Activity of Natural Killer Cells 5.1. Analysis of Anticancer Activity in Ovarian Cancer Animal Model Anticancer activity of the natural killer cells according to one specific embodiment was examined in vivo.

First, $1 \times 10^7$ cells/head of OVCAR3, which is an ovarian cancer cell line, was subcutaneously administered to NOD-SCID mice to prepare xenograft animal models. Thereafter, experimental groups were set up as shown in Table 7 below.

TABLE 7

| No. | Group | Dosage | Administration route | Note |
|---|---|---|---|---|
| 1 | G1 Vehicle | 5% albumin: dextran infusion = 1:1, 100 μl | i.v. | Negative control |
| 2 | G2 Cisplatin | Cisplatin 1.5 mg/kg | i.p. | Positive control |
| 3 | G3 NK Live | $1 \times 10^7$ cells/head | i.v. | Fresh NK cells |
| 4 | G4 NK Freeze | $1 \times 10^7$ cells/head | i.v. | Frozen NK cells |

A negative control G1 vehicle group was prepared at a ratio of 5% albumin:dextran infusion=1:1, and 100 μl thereof was intravenously administered. A positive control G2 cisplatin group received 1.5 mg/kg of cisplatin. Natural killer cell-administered groups include G3 NK Live group and G4 NK Freeze group, which differ from each other in terms of fresh and frozen cells. With regard to G4 NK Freeze group, frozen NK cells were thawed, and $1 \times 10^7$ cells thereof was administered to each animal. With regard to G3 NK Live group, cells were collected during culture, and $1 \times 10^7$ cells thereof was administered to each animal. The administration group was administered twice a week for a total of 6 times. During the test period, the survival rate, tumor size, and symptoms of the mice were observed. Monitoring was performed for 78 days. After 78 days, the animals were sacrificed, and the weight of the extracted tumor was measured. The results are shown in Table 8 below and FIG. 11.

TABLE 8

| Group | Tumor weight (mean, g) |
|---|---|
| G1 | 1.74 ± 0.27 |
| G2 | 1.15 ± 0.10 |
| G3 | 0.49 ± 0.07 |
| G4 | 0.57 ± 0.09 |

Figure 11:
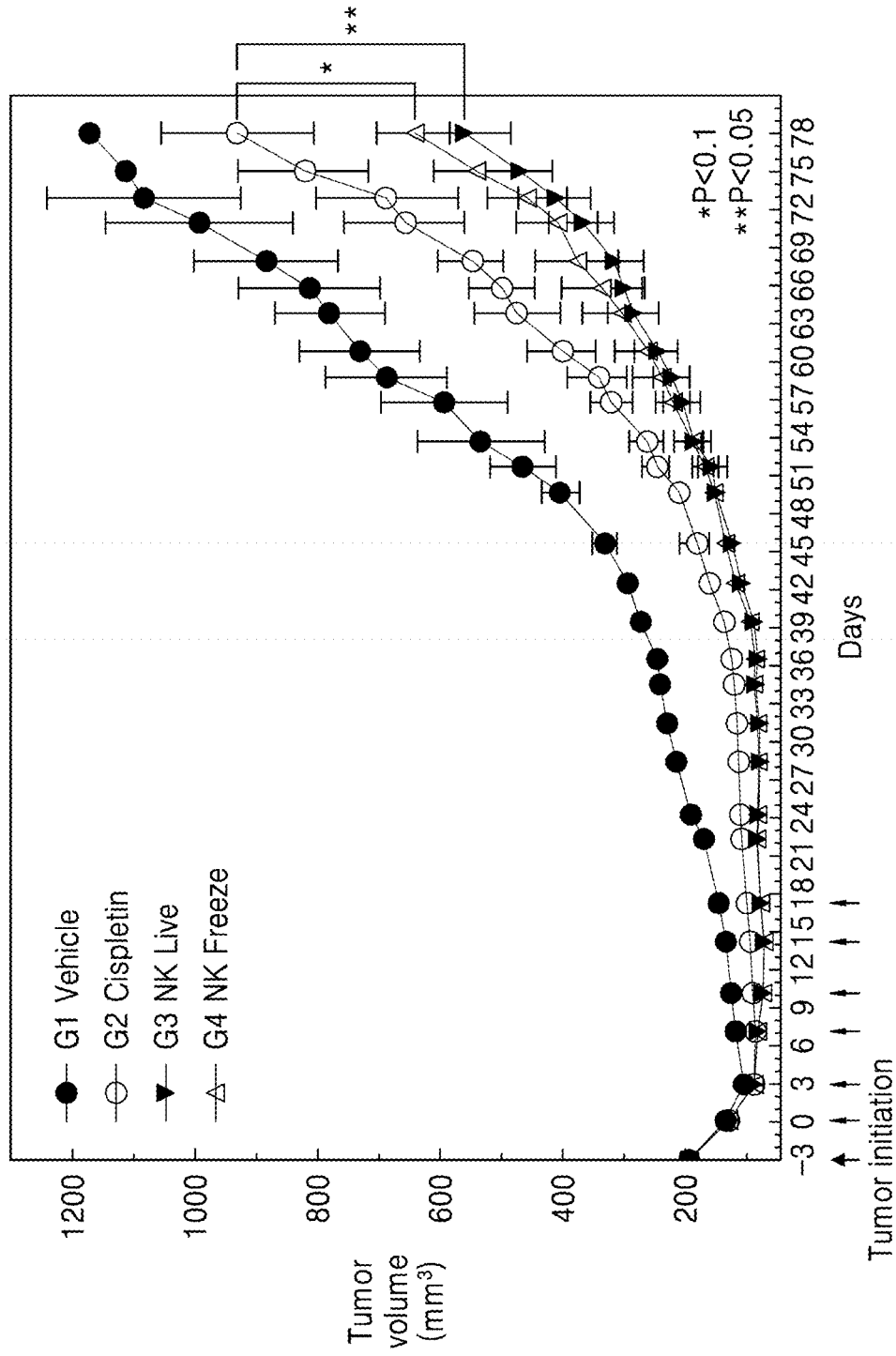
FIG. 11 shows a graph showing a reduction in the tumor weight after administering natural killer cells according to one specific embodiment to ovarian cancer animal models (arrows indicate the time of drug administration)

FIG. 11 shows a graph showing a reduction in the tumor weight after administering the natural killer cells according to one specific embodiment to ovarian cancer animal models (arrows indicate the time of drug administration).

As shown in Table 8 and FIG. 11, it was confirmed that when the natural killer cells according to one specific embodiment were administered, the weight of the tumor was reduced by about 50% to about 60%, as compared with that of the positive control group. In particular, in the positive control group, tumor growth was accelerated after 50 days, and the tumor volume rapidly increased, whereas in the group administered with the natural killer cells according to one specific embodiment, tumor growth was remarkably delayed during the monitoring period.

5.2. Analysis of Anticancer Activity in Stomach Cancer Animal Model

Anticancer activity of the natural killer cells according to one specific embodiment was examined in vivo.

First, $1\times10^6$ cells/head of NCI-N87, which is a stomach cancer cell line, was administered to NOD-SCID mice to prepare xenograft animal models. 6 days after tumor transplantation, experimental groups were set up as shown in Table 9 below.

TABLE 9

| No. | Group | Dosage | Administration route | Note |
|---|---|---|---|---|
| 1 | G1 Vehicle | 5% albumin: dextran infusion = 1:1, 200 μl | i.v. | Negative control |
| 2 | G2 HER2 | Herceptin 1 mg/kg | i.p. | Positive control |
| 3 | G3 NK Live | $1 \times 10^7$ cells/head | i.v. | Fresh NK cells |
| 4 | G4 NK Freeze | $1 \times 10^7$ cells/head | i.v. | Frozen NK cells |
| 5 | G5 NK L + Herceptin | $1 \times 10^7$ cells/head + Herceptin | i.v. | Fresh NK cells + Herceptin |
| 6 | G6 NK F + Herceptin | $1 \times 10^7$ cells/head + Herceptin | i.v. | Frozen NK cells + Herceptin |

A negative control G1 vehicle group was prepared at a ratio of 5% albumin:dextran infusion=1:1, and 200 μl thereof was intravenously administered. A positive control G2 HER2 group received 1 mg/kg of Herceptin twice a week for a total of 6 times. G3 NK Live group and G4 NK Freeze group, which were groups administered with the natural killer cells alone, were intravenously administered with $1\times10^7$ cells/head twice a week for a total of 6 times. With regard to G3 NK Live group, cells obtained by recovering the cells during culture were administered thereto. With regard to G4 NK Freeze group, frozen NK cells were thawed, and $1\times10^7$ cells/head thereof was administered thereto. G5 NK L+Herceptin group and G6 F+Herceptin group, which were groups co-administered with NK cells and Herceptin, were intravenously administered with the same cells as in the group administered with NK cells alone, in combination with 1 mg/kg of Herceptin, twice a week for a total of 6 times.

During the test period, the survival rate, tumor size, and symptoms of the mice were observed. Monitoring was performed for 52 days. After 52 days, the animals were sacrificed, and the weight of the extracted tumor was measured. The results are shown in Table 10 below and FIG. 12.

TABLE 10

| Group | G1 Vehicle | G2 HER2 |
|---|---|---|
| Tumor weight (mean, g) | 3.38 ± 0.22 | 2.99 ± 0.28 |
| Group | G3 NK live | G4 NK freeze |
| Tumor weight (mean, g) | 1.15 ± 0.23 | 1.28 ± 0.23 |
| Group | G5 NK L + HER2 | G6 NK F + HER2 |
| Tumor weight (mean, g) | 0.64 ± 0.15 | 0.68 ± 0.23 |

Figure 12:
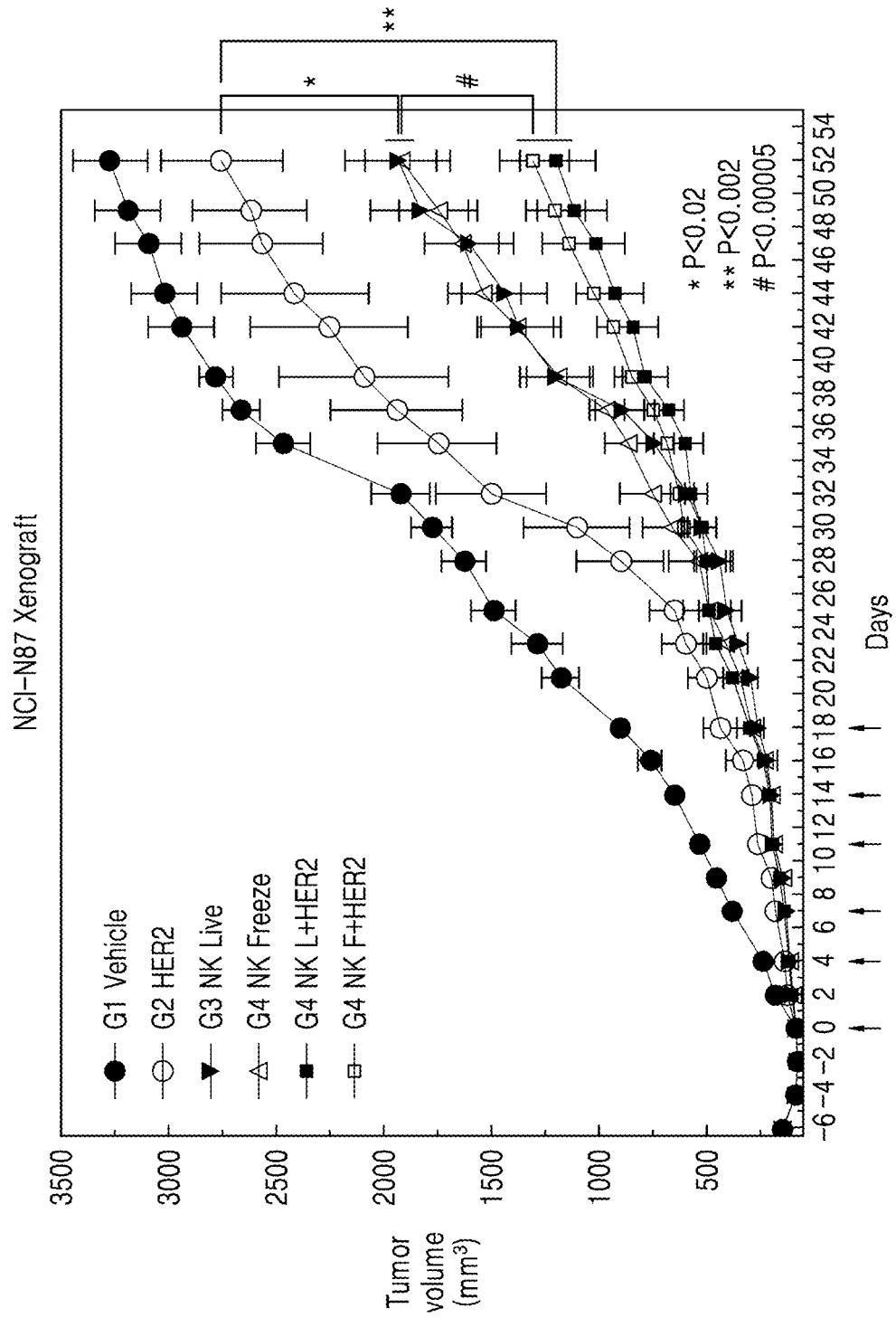
FIG. 12 shows a graph showing a reduction in the tumor weight after administering natural killer cells according to one specific embodiment to stomach cancer animal models (arrows indicate the time of drug administration)

FIG. 12 shows a graph showing a reduction in the tumor weight after administering the natural killer cells according to one specific embodiment to stomach cancer animal models.

As shown in Table 10 and FIG. 12, it was confirmed that when the natural killer cells according to one specific embodiment were administered, the weight of the tumor was reduced by about 60% to about 70%, as compared with that of the positive control group. In particular, in the positive control group, tumor growth was accelerated after 28 days, and the tumor volume rapidly increased, whereas in the group administered with the natural killer cells according to one specific embodiment, tumor growth was remarkably delayed during the monitoring period.

It was also confirmed that when Herceptin and the natural killer cells were co-administered, the weight of the tumor was reduced by about 17% to about 20%, as compared with that of the group administered with the natural killer cells alone. This means that antibody-dependent cell cytotoxicity (ADCC) by co-administration of the natural killer cells and Herceptin may provide high tumor growth inhibitory effect and a maintenance period of anticancer efficacy.

5.3. Analysis of Anticancer Activity in Glioblastoma Animal Model

Anticancer activity of the natural killer cells according to one specific embodiment was examined in vivo.

First, $1\times10^4$ U87MG-luci cells obtained by transducing a luciferase gene into a human brain glioblastoma-derived cell line U87MG were transplanted into the right brain cerebral hemisphere skull of 7-week-old NOG female mouse to construct an experimental orthotopic animal model. At a predetermined period of time after cell transplantation, Bioluminescence (BLI) of the tumor was measured using an IVIS bio-imaging equipment (PerkinElmer, USA), and subjects were selected such that the BLI value had an average value on the $7^{th}$ day after transplantation. The selected animals were divided according to experimental groups, as shown in Table 11 below.

TABLE 11

| No. | Group | Dosage | Administration route | Note |
|---|---|---|---|---|
| 1 | G1 Vehicle | 5% albumin: dextran infusion = 1:1, 200 μl | i.v. | Negative control |
| 2 | G2 NK cells | $1 \times 10^6$ cells/head | i.v. | Experimental group |

A negative control G1 vehicle group was prepared at a ratio of 5% albumin:dextran infusion=1:1, and 200 μl thereof was intravenously administered to each animal. An experimental G2 NK cell group was intravenously administered with the natural killer cells at a dose of $1\times10^6$ cells/head twice a week for a total of 6 times. During the monitoring period, an IVIS bioimaging system (perkinelmer, U.S.A.) was used to measure the tumor volume twice a week. To measure the tumor volume, 150 mg/kg of luciferin (promega) was intraperitoneally administered at a dose of 10 mL/kg. After 10 minutes, each individual thus administered was sequentially anesthetized using an inhalation anesthetic. For the individuals fully anesthetized, bioluminescence (BLI) of the tumor was sequentially measured using the IVIS system, and the measured bioluminescence value of the region of interest (ROI) was analyzed according to Threshold corresponding to the internal standard of a committed research institute, Woojung Bio (Gyeonggi-do, Korea). The results are shown in Table 12 below and FIG. 13.

TABLE 12

| Group | | Bioluminescence (p/sec/cm²/sr) Time after administration (day) | | | | | |
|---|---|---|---|---|---|---|---|
| | | 1 | 3 | 7 | 9 | 13 | 16 |
| G1 Dosage: 0 cell/0.2 mL/head | Mean S.E. N | 4.28.E+08 7.61.E+07 5 | 1.14.E+09 3.41.E+08 5 | 4.43.E+09 1.00.E+09 5 | 2.98.E+09 5.90.E+08 5 | 6.10.E+09 1.21.E+09 5 | 1.09.E+10 2.94.E+09 5 |
| G2 Dosage: 1 × 10⁶ cells/ 0.2 mL/head | Mean S. E. N | 3.19.E+08 8.28.E+07 5 | 5.70.E+08 1.52.E+08 5 | 5.19.E+09 1.35.E+09 5 | 2.58.E+09 7.16.E+08 5 | 3.17.E+09 1.40.E+09 5 | 1.78.E+09 7.69.E+08 5 |

Each number represents mean+S.E. (n=5) S.E.: Standard error N: Number of animals FIG. 13 shows a graph showing a reduction in the tumor weight after administering natural killer cells according to one specific embodiment to glioblastoma animal models.

Figure 13:
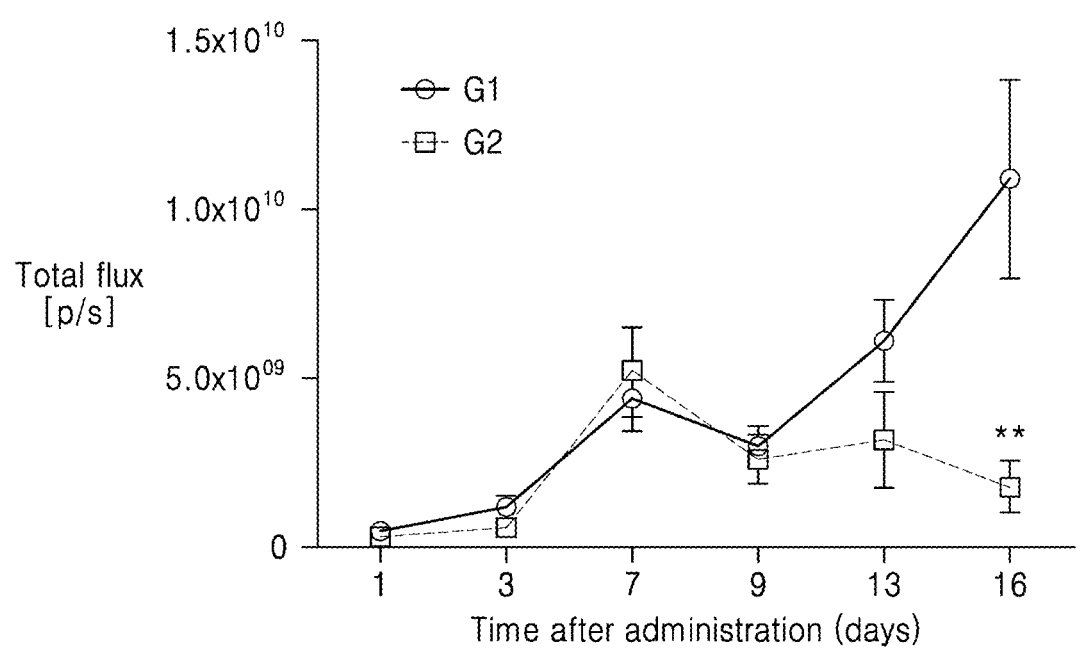
FIG. 13 shows a graph showing a reduction in the tumor weight after administering natural killer cells according to one specific embodiment to glioblastoma animal models.

As shown in Table 12 and FIG. 13, the negative control group (G1) exhibited a change in tumor volume from 4.28.E+08 p/sec/cm²/sr to 1.09.E+10 p/sec/cm²/sr until 16 days after administration, indicating a continuous increase during the experimental period. In contrast, when the natural killer cells according to one specific embodiment were administered, the tumor volume increased from 3.19.E+08 p/sec/cm²/sr to 1.78.E+09 p/sec/cm²/sr, indicating an almost insignificant increase during the experimental period, and showing the difference in the tumor weight about 5 times, as compared with that of the negative control group, on the 16$^{th}$ day. This means that the natural killer cells according to one specific embodiment have a high tumor growth inhibitory effect on glioblastoma.

The invention claimed is:

1. A method of treating cancer, the method comprising administering an effective amount of an isolated natural killer cell, wherein the natural killer cell has:
   (1) an expression level of a KIR2DS4 gene on day 14 of culture which is 10 times to 50 times higher compared with that on day 0 of peripheral blood mononuclear cell (PBMC) culture; and
   (2) one or more characteristics selected from the following (a) to (e) or a population thereof to an individual in need thereof:
      (a) a relative mean fluorescence intensity (MFI) value of NKG2D exhibits a 1.2-fold to 12-fold increase, as compared with that on day 0 of PBMC culture;
      (b) a relative MFI value of NKp30 exhibits a 1.5-fold to 15-fold increase, as compared with that on day 0 of PBMC culture;
      (c) a relative MFI value of NKp44 exhibits a 12-fold to 22-fold increase, as compared with that on day 0 of PBMC culture;
      (d) a relative MFI value of integrin subunit alpha 1 (ITGA1) exhibits a 1.8-fold to 25-fold increase, as compared with that on day 0 of PBMC culture; and
      (e) a relative MFI value of integrin subunit alpha 2 (ITGA2) exhibits a 1.4-fold to 6-fold increase, as compared with that on day 0 of PBMC culture;
   wherein the relative MFI is defined by the following Equation 1:

Relative MFI=Receptor MFI/Isotype MFI.  [Equation 1]

2. The method of claim 1, wherein the natural killer cell (i) promotes immune activation, blood-brain barrier penetration, or cell migration; or (ii) inhibits self-tolerance.

3. The method of claim 1, wherein the cancer is one or more selected from the group consisting of lung cancer, laryngeal cancer, stomach cancer, colorectal cancer, rectal cancer, liver cancer, gallbladder cancer, pancreatic cancer, breast cancer, ovarian cancer, uterine cancer, cervical cancer, prostate cancer, kidney cancer, skin cancer, bone cancer, muscle cancer, fat cancer, fibrous cell carcinoma, blood cancer, leukemia, lymphoma, multiple myeloma, and glioma.

4. The method of claim 3, wherein the glioma is astrocytic tumor, oligodendroglial tumor, mixed glioma, or ependymal tumor.

5. The method of claim 4, wherein the astrocytic tumor is glioblastoma, anticancer drug-resistant glioblastoma, or recurrent glioblastoma.

6. The method of claim 1, wherein the cancer secretes or expresses MHC class I polypeptide-related sequence A (MICA) or platelet-derived growth factor-DD (PDGF-DD).

7. The method of claim 1, wherein
   the relative MFI value of (a) exhibits a 3-fold to 6-fold increase;
   the relative MFI value of (b) exhibits a 3-fold to 6-fold increase;
   the relative MFI value of (c) exhibits a 12-fold to 18-fold increase;
   the relative MFI value of (d) exhibits a 6-fold to 10-fold increase; and
   the relative MFI value of (e) exhibits a 2-fold to 4-fold increase.

8. The method of claim 1, wherein the natural killer cell further has one or more characteristics selected from CD16 having an MFI value of 10 to 140, LFA-1 having an MFI value of 20 to 160, NKG2D having an MFI value of 5 to 25, NKp30 having an MFI value of 5 to 20, NKp44 having an MFI value of 12 to 25, ITGA1 having an MFI value of 4 to 25, and ITGA2 having an MFI value of 2 to 10.

9. The method of claim 1, wherein the natural killer cell further has one or more characteristics selected from CD2 having an MFI value of 20 to 180, CD27 having an MFI value of 0.1 to 1.5, CD69 having an MFI value of 1 to 10, CD226 having an MFI value of 2 to 12, NKp46 having an MFI value of 2 to 8, CD160 having an MFI value of 0.1 to 4, KIR2DL1 having an MFI value of 0.1 to 4, KIR2DL3 having an MFI value of 0.1 to 5, KIR3DL1 having an MFI value of 0.1 to 4, NKG2A having an MFI value of 0.4 to 16, CD161 having an MFI value of 0.2 to 12, CCR3 having an MFI value of 0.3 to 3, CCR5 having an MFI value of 0.5 to 4, CCR6 having an MFI value of 0.8 to 6, CXCR3 having an MFI value of 0.4 to 5, CXCR1 having an MFI value of 0.4 to 5, CXCR2 having an MFI value of 0.1 to 3, and ITGB7 having an MFI value of 1 to 16.

10. The method of claim 1, wherein the natural killer cell further has any one characteristic selected from KIR2DS1+, KIR2DS2+, KIR2DS3+, CXCR1+, CXCR2+, CXCR3+, CCR3+, CCR5+, CCR6+, PSA-NCAM+, nestin+, tyrosine hydroxylase+, CD147+, CD127+, CD15+, CD31+, CD146+, CD49c+, CD107a+, NKG2A+, CD45+, CD44−, CD140a+, CD87−, CD11b+, CD10−, and CD80 −.

11. The method of claim 1, wherein 50% to 90% of the population expresses NKp44; 50% to 90% of the population expresses KIR2DS2; or 60% to 100% of the population expresses NKG2D.

12. The method of claim 1, wherein the natural killer cell is treated with PDGF-AA, PDGF-BB, PDGF-CC, PDGF-DD, or PDGF-AB, when cultured from PBMC.

* * * * *